United States Patent [19]

Charlton et al.

[11] Patent Number: 4,649,123
[45] Date of Patent: Mar. 10, 1987

[54] ION TEST MEANS HAVING A HYDROPHILIC CARRIER MATRIX

[75] Inventors: Steven C. Charlton; Paul Hemmes, both of Elkhart; Arthur L. Y. Lau, Mishawaka, all of Ind.

[73] Assignee: Miles Laboratories, Inc., Elkhart, Ind.

[21] Appl. No.: 751,257

[22] Filed: Jul. 2, 1985

Related U.S. Application Data

[63] Continuation-in-part of Ser. No. 493,982, May 12, 1983, abandoned.

[51] Int. Cl.[4] .................. G01N 21/78; G01N 33/52
[52] U.S. Cl. ........................ 436/79; 422/56; 427/2; 436/74; 436/170; 436/172; 436/175
[58] Field of Search .............. 422/56, 57, 58; 436/73, 436/74, 79, 172, 175, 169, 170; 427/2

[56] References Cited

U.S. PATENT DOCUMENTS

| | | | |
|---|---|---|---|
| 3,616,251 | 10/1971 | Lecco et al. | 422/56 X |
| 3,635,679 | 1/1972 | Bloch et al. | 436/169 X |
| 3,992,158 | 11/1976 | Przybylowicz et al. | 422/58 X |
| 4,003,707 | 1/1977 | Lubbers et al. | |
| 4,061,468 | 12/1977 | Lange et al. | 422/56 |
| 4,272,484 | 6/1981 | Lubbers | 422/68 |
| 4,272,485 | 6/1981 | Lubbers | 422/68 |
| 4,356,149 | 10/1982 | Kitajima et al. | 422/57 X |
| 4,367,072 | 1/1983 | Vogtle et al. | 436/501 |
| 4,540,520 | 9/1985 | Charlton et al. | 260/396 N |
| 4,552,697 | 11/1985 | Yip et al. | 260/396 N |
| 4,557,900 | 12/1984 | Heitzmann | 422/56 X |

FOREIGN PATENT DOCUMENTS 0041175 12/1981 European Pat. Off.
2842862 4/1980 Fed. Rep. of Germany ........ 436/74

OTHER PUBLICATIONS

Feinstein et al., Proc. Nat. Acad. Sci., USA, vol. 68, No. 9, pp. 2037–2041, Sep. 1971.
Kusnir et al., Chemical Abstracts, vol. 82, No. 51257q, 1975.
Sumiyoshi et al., Chemical Abstracts, vol. 89, 1978, No. 89:55833s.

*Primary Examiner*—Arnold Turk
*Attorney, Agent, or Firm*—Mary G. Boguslaski

[57] ABSTRACT

A test means for determining the presence of an ion in an aqueous test sample, a method for preparing it and a method for using it. The test means comprises a hydrophilic carrier matrix incorporated with finely divided globules of a hydrophobic vehicle. The hydrophobic vehicle contains an ionophore capable of forming a complex with the ion and a reporter substance capable of interacting with the complex of ionophore and ion to produce a detectable response. The test means of this invention is useful for clinical determinations of serum potassium. The test means forms the reagent layer in a multilayer format which is particularly suited to whole blood electrolyte determinations and does not require washing or wiping before use.

33 Claims, 13 Drawing Figures

ION TEST MEANS HAVING A HYDROPHILIC CARRIER MATRIX

CROSS REFERENCE TO RELATED APPLICATIONS

This application is a continuation-in-part of U.S. Ser. No. 493,982, filed May 12, 1983, now abandoned.

1. INTRODUCTION

The present invention relates to the measurement of ions, in particular ions in aqueous solution, and to a test means or device for performing such measurements. The invention provides a convenient format for determining the presence and/or concentration of ions whereby results are available shortly after contacting an aqueous test sample with the test means or device. Cumbersome, expensive electronic equipment such as ion-specific electrodes, flame photometers, atomic absorption spectrophotometers or the like is not needed. The present invention enables the user merely to contact the test sample with the test device, or similar test means configuration, and determine any detectable response.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function and conditions such as oliguria, anuria, urinary obstruction and renal failure due to shock. The measurement of potassium in serum is particularly important clinically. The measurement requires high sensitivity and precision since the normal clinical range is only from about 2 to about 10 millimolar (mM) with a normal range from about 3.5 to 5.5 mM. Measurement of lithium levels in the blood is also important since the toxic dose levels are only slightly higher than the therapeutic levels used in psychiatric treatment.

A sensitive, convenient and inexpensive method for determining ion concentration would greatly enhance the state of these technologies, as well as any others where such rapid, accurate determinations would be beneficial. Thus, for example, if a medical laboratory technician could accurately measure the sodium, lithium, potassium, magnesium or calcium level of a serum or whole blood sample in a matter of seconds or minutes, such rapid results would increase laboratory efficiency and aid the physician in diagnosis.

2. BACKGROUND OF THE INVENTION

Methods for determining ions in solution include flame photometry, atomic absorption photometry and ion-specific electrodes. Test strip formats have been disclosed in copending U.S. patent application Nos. 493,969; 493,982; 493,983; and 583,127 assigned commonly herein. The use of certain compounds and compositions which selectively isolate ions from a sample solution has become popular in ion-specific electrodes. These compounds, known as ionophores, have the capability of transporting ions into an electrode membrane causing a difference in potential which can be measured. Ion assays utilizing the ion/ionophore phenomenon include membrane electrodes, liquid/liquid partitioning, fluorescence and test strips.

2.1 Ion-Specific Electrodes

When two solutions having different concentrations of ions are separated by an electrically conductive membrane, an electrical potential (EMF) is generated. In membrane separation cells, the membrane can be a simple fritted glass barrier, allowing a small but measurable degree of ion diffusion from one solution to the other. Alternatively, a nonporous, electrically nonconductive film, such as polyvinyl chloride, impregnated with an ionophore can be employed. In the absence of the ionophore, the film is an insulator and no EMF can be measured; when blended with an ionophore, charged ions are bound to the film and a small, measurable current can be induced to flow. Because the ionophore is selective in its affinity, and thus will bind only certain specific ions, such cells are ion selective. Any measurable EMF is due solely to the presence of the bound ions.

The current flowing across the membrane is so small that the actual quantity of the ion or its counterion transported is insignificant. Electrical neutrality of the membrane is maintained either by a reverse flow of hydrogen ions, or by a parallel flow of hydroxyl ions. This anion affect can reduce the specificity of the electrode towards the specific ion to be determined and is an interference to be minimized.

A major difficulty in the use of such ion-selective electrodes has been the marked reduction of accuracy and speed of response over time. Further, small changes in ion concentration produce such small changes in EMF that sophisticated voltmeter equipment is required.

It has been known that certain antibiotics, such as valinomycin, have an effect on the electrical properties of phospholipid bilayer membranes (biological membranes) such that these antibiotics solubilize cations within the membrane in the form of mobile charged couples, thereby providing a "carrier" mechanism by which cations can cross the insulating hydrocarbon interior of the membrane. Such complexes carry charge through the membrane such that a voltage differential can be determined between solutions on either side of the membrane.

U.S. Pat. No. 3,562,129 issued to Simon, describes the use of porous membranes impregnated with macrocyclic derivatives of amino and oxy-acids in ion-sensitive electrodes. Materials used to form the membrane are glass frits and other porous membranes. Such electrodes are said to be effective in measuring ion activities.

U.S. Pat. No. 4,053,381, issued to Hamblen, at al., discloses similar technology, and utilizes an ion-specific membrane having ion mobility across it.

U.S. Pat. No. 3,957,607 issued to Simon et al., discloses a process for the electrochemical determination of cations utilizing an electrode having a membrane containing neutral ionophores capable of forming lipid soluble complexes with cations.

2.2 Liquid/Liquid Partitioning

Another known application of ionophores in ion determinations is through liquid/liquid partitioning. In this procedure, a hydrophobic ionophore is dissolved in an organic solvent immiscible with water. Eisenman et al., *Membrane Biol.*, 1:294–345 (1969) disclose the selective extraction of cations from aqueous solutions into organic solvents by macrotetralide actin antibiotics. This technique involves shaking an organic solvent phase containing the antibiotics with aqueous solutions containing cationic salts of lipid-soluble, colored anions, such as picrates and dinitrophenolates. The intensity of color developed in the organic phase is then measured spectrophotometrically to indicate how much salt has been extracted. Phase transfer has also been studied by Dix et al., *Angew. Chem. Int. Ed. Engl.*, 17S:857 (1978) and in reviews including Burgermeister et al., *Top Curr. Chem.*, 69:91 (1977); Yu et al., "Membrane Active Complexones," Elsevier, Amsterdam (1974); and Duncan, "Calcium in Biological Systems," Cambridge University Press (1976).

Sumiyoshi, et al., *Talanta*, 24, 763–765 (1977) describes a method for determining potassium ion in serum. In this technique serum is deproteinated by trichloroacetic acid and an indicator dye is added and shaken with a solvent such as chloroform containing valinomycin.

Partitioning of a compound is rapid and effective between liquids, as shown by Eisenman, because of the mobility of the ionophore carrier and ions, which allows the transported species to diffuse rapidly away from the interface. Such a mechanism is normally impossible in the solid phase because of rigidity, immobility and essentially zero diffusion of materials in a solid phase.

2.3 Fluorescent Anions

Yet another approach to the measurement of ion activity in aqueous solutions utilizes fluorescent anions. Feinstein, et al., *Proc. Nat. Acad. Sci. U.S.A.*, 68, 2037–2041 (1971). It is stated that the presence of cation/ionophore complexes in organic solvents are known, but that complex formation in purely aqueous media had theretofore not been detected. Feinstein, et al., demonstrated the existence of such complexes in water through the use of the fluorescent salts, 1-anilino-8-naphthalene sulfonate and 2-p-toluidinyl sulfonate.

It was found that interaction of the cation/ionophore complexes with the fluorescent dyes produced enhanced fluorescence emission, increased lifetime and polarization, and significant blue-shift at the emission maxima of the fluorescence spectrum. At constant concentrations of ionophore and fluorophore, the intensity of fluorescence emission was found to be a function of cation concentration.

2.4 Chromophore-labeled Ionophore

The ion assay disclosed in U.S. Pat. No. 4,367,072 is primarily directed toward the use of a a chromogenic ionophore, i.e., an ionophore covalently linked to a chromogen. A charged chromogen-ionophore complex having the same charge as the ion to determined is also used. In use, a chromogenic ionophore or charged chromogen-ionophore complex is added to a liquid sample and the color of the solution is monitored spectrophotometrically. Mention is made of incorporating the ionophore into a carrier such as paper, synthetic resin film, silicon oxide, natural or synthetic fibers or metal.

2.5 Test Strip Formats

Test strip formats for the determining the presence of an ion in an aqueous test sample have been disclosed in copending U.S. Ser. No. 493,969, 493,982, 493,983 and 583,127 assigned commonly herein.

2.6 Multilayer Formats

Multilayer formats for the determination of analytes by chemical reaction of the analyte with the components in the reagent layer have been disclosed (see for example U.S. Pat. No. 3,992,158 to Przybylowicz et al). Kitajima et al. in U.S. Pat. No. 4,356,149 discloses a multilayer integral element for the chemical analysis of blood wherein the reagent layer is composed of a hydrophilic binder and fine hydrophobic particles dispersed in that binder, which particles contain the reagent capable of producing a color change with the component being analyzed. U.S. Pat. No. 4,356,149 to Kitajima et al. is directed toward eliminating extra layers made necessary by incompatible reagent components. Kitajima deals only with the determination of a neutral analyte with a reaction requiring the separation of incompatible reagent components. U.S. Pat. No. 4,255,384, to Kitajima et al. concerns a multilayer integrated element for the chemical analysis of blood.

2.7 Summary

Many methods are known for assaying ions in solution. Instrumental methods include such sophisticated techniques as ion-specific potentiometry, flame photometry and atomic absorption photometry. The use of ionophores which selectively complex with specific ions has led to five basic approaches: ion selective electrodes, liquid/liquid partitioning, fluorescence enhancement, chromophore-labeled ionophore conjugates and test strips.

Prior to the invention claimed herein, none of the approaches, however, gave the user accurate and sensitive analysis results through contacting a test sample with a test means or device. The present invention, on the other hand, permits the user merely to contact the sample with the test means or device and observe a change in color or other detectable response.

3. BRIEF DESCRIPTION OF THE DRAWINGS

Performance data depicting dose/response measurements in (K/S) or (K/S)$^2$ versus millimolar (mM) potassium ion concentration [K+], of various embodiments of the present invention is portrayed graphically in FIGS. 1 to 8. The experiments in which the data was generated are described in Section 11 herein, entitled "Examples". FIG. 8 depicts dose/response data for serum potassium with a device of the present invention over the clinically significant concentration range versus the concentration found by flame photometry. The symbol [K+] denotes millimolar potassium ion concentration. FIG. 9 diagrammatically depicts a multilayer device format particularly suited for whole blood determinations. FIG. 9b depicts a supported two layered device; FIG. 9a depicts a supported three layer device.

4. SUMMARY OF THE INVENTION

Figure 1:
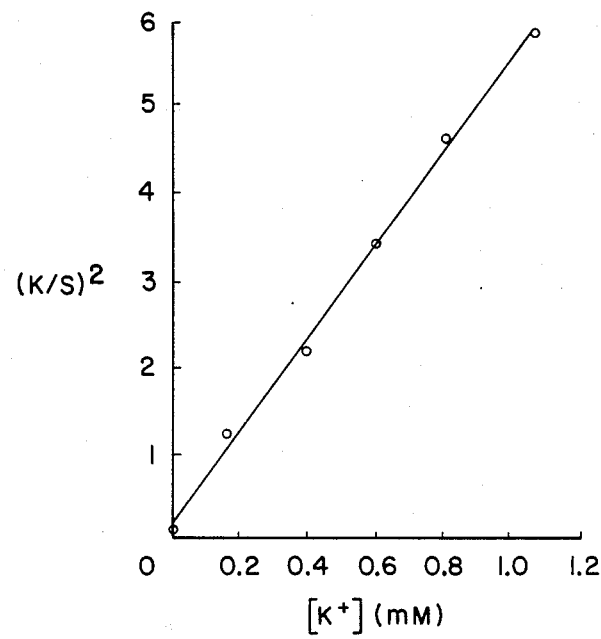

This invention resides in the discovery of a new test means for detecting the presence of an ion in an aqueous test sample and determining its concentration. The test means comprises a hydrophilic carrier matrix incorporated with finely divided globules of a hydrophobic vehicle containing two principal ingredients: an ionophore capable of forming a complex with a specific ion to be determined and a reporter substance capable of interacting with the complex of the ionophore and the ion to produce a detectable response such as a change in, or the appearance of, color or fluorescence.

A preferred embodiment is a multilayer format in which the test means forms the reagent layer of a multilayer test device. In the multilayer format a transparent support member is used.

In use the sample is contacted with the test means (or device) and the presence and/or concentration of the ion is then determined by observing any detectable response produced. The single layer test means (or device) is particularly useful for a serum potassium ion determination. The multilayer format is preferred for whole blood determinations, as electrolytes can be determined without washing or wiping the device.

The test means and device of the present invention provide rapid results, sufficient detectable response forming in most instances in at least a few minutes. No cumbersome, expensive testing equipment is required. The response can be of sufficient magnitude to enable direct visual detection. Moreover, it has been found that the color or other response produced in the test means is usually stable, in some instances for a period of days, such that a number of used test means can be set aside for reading at some future time.

5. DEFINITIONS

The following definitions are provided to clarify the scope of the present invention and to enable its formulation and use.

5.1 The term "ionophore" includes molecules capable of selectively forming a complex with a particular ion in a nonpolar environment to the substantial exclusion of others. For example the cyclic polyether 2,3-naphtho-1,4,7,10,13-pentaoxacyclopentadeca-2-ene (sometimes known as 2,3-naphtho-15-crown-5 and called Potassium Ionophore I herein) binds to potassium ions selectively to form a cationic complex. Included in the term are coronands, such as are crown ethers, cryptands, podands and antibiotic type ionophores such as valinomycin and macrotetralide actins.

5.2 A "reporter substance" is one which is capable of interacting with an ionophore/ion complex to produce a change in, or appearance of, color or other detectable response. Preferred reporters are neutral compounds having a dissociable proton, which is capable of dissociating upon interaction of the reporter with the ionophore/ion complex to produce a detectable response. With the loss of a proton, the reporter becomes charged, effecting a change in electron distribution. The change in electron distribution produces a detectable response. The expression "reporter substance" includes phenolic compounds, such as p-nitrophenol, which are relatively colorless in the nonionized state, but which color upon ionization, and fluorescent compounds which produce more or less fluorescence upon a change in electron distribution. The reporter substance can also be one which can trigger a detectable response together with other components. For example, the change in electron distribution in the reporter substance caused by interaction with the complex can in turn facilitate the interaction of the reporter with another component which would then produce a detectable response.

5.3 By "interacting" is meant any coaction between a reporter substance and an ionophore/ion complex which leads to a detectable response. The interaction between an ionophore/cation complex and preferred reporters having a dissociable proton will cause the reporter to lose a proton thus producing a detectable response. An example of the reporter substance interacting with the complex is the case where the reporter is changed by the complex from a colorless to a colored state, such as in the case of p-nitrophenol.

5.4 The expression "detectable response" is used herein as a change in, or occurrence of, a parameter in a test means system which is capable of being perceived, either by direct observation or instrumentally, and which is a function of the presence of a specific ion in an aqueous test sample. Some detectable responses are the change in, or appearance of, color, fluorescence, reflectance, pH, chemiluminescence and infrared spectra.

5.5 By the expression "intermediate alkyl" as used herein is meant an alkyl group having from about 5 to about 15 carbon atoms. It includes normal and branched isomers. It can be unsubstituted or it can be substituted, provided any such substitution not interfere with the operation of the test means.

5.6 By the expression "lower alkyl", as used in the present disclosure, is meant an alkyl moiety containing about 1 to 4 carbon atoms. Included in the meaning of lower alkyl are methyl, ethyl, n-propyl, isopropyl, n-butyl, sec-butyl and tert-butyl. These can be unsubstituted, or they can be substituted provided any such substituents not interfere with the operation of the test means.

5.7 By "pseudohalogen" is meant atoms or groups of atoms which, when attached to an unsaturated or aromatic ring system, affect the electrophilicity or nucleophilicity of the ring system, and/or have an ability to distribute an electrical charge through delocalization or resonance, in a fashion similar to the halogens. Thus, whereas halogen signifies Group VII atoms such as F, Cl, and I, pseudohalogens embrace such moieties as —CN, —SCN, —OCN, —N$_3$, —COR, —COOR, —CONHR, —CF$_3$, —CCl$_3$, —NO$_2$, —SO$_2$CF$_3$, —SO$_2$CH$_3$, —SO$_2$C$_6$H$_5$, —SO$_2$C$_6$H$_4$CH$_3$, —SOC$_6$H$_5$, and —SOCF$_3$ in which R is alkyl or aryl.

5.8 The term "globule" as used herein refers to spherical or quasi-spherical globes, balls or other shaped particles of a substance such as form in biphasic suspensions or emulsions. When an oil-in-water suspension or emulsion is formed, the oil (hydrophobic) phase exists as spherical entities surrounded by a more or less continous aqueous phase. The more energy supplied in forming the suspension, the smaller the size of the globules. Likewise, the globular size can be controlled by additives such as detergents and other emulsifying agents.

Also included in the meaning of the term "globule" are finely divided particles of a solid material. Thus, where the hydrophobic vehicle is a nonporous, nonpolar materials such as a polymer, it can be ground or otherwise finely divided into solid particles.

5.9 By "hydrophilic" is meant that characteristic of a substance to have a strong or pronounced tendency to bind or absorb water. Included in the term are those materials which undergo swelling or formation of reversible gels with water, or which are wettable or permeable by water, or which form aqueous solutions.

6. THE TEST MEANS

The test means comprises a hydrophilic carrier matrix incorporated with finely divided globules of a hydrophobic vehicle, the globules containing an ionophore and a reporter substance. When an aqueous test sample contains an ion capable of complexing with the ionophore, the ion can enter the hydrophobic globules and interact with the reporter substance, thereby producing a detectable response.

6.1 The Carrier Matrix

In order for the test means to provide a detectable response to a specific ion, it is necessary that the aqueous test sample have substantially unimpeded access to the outer surface of the hydrophobic globules. Thus, the carrier matrix with which the globules is incorporated must be easily wetted by aqueous systems, i.e., hydrophilic.

Typical of some materials which display suitable hydrophilicity are gelatin, agarose, poly(vinyl alcohol), copolymers of acrylic acid, poly(propyleneimine), carrageenan and alginic acid. These are water-soluble polymers which in their dry state exhibit a marked wettability by aqueous media.

Other insoluble polymeric materials suitable for use include porous substances, such as paper and other cellulosic systems, sintered ceramic frits and similar porous, hydrophilic matrices, provided the integrity of the globules can be maintained. Thus, for example, a suitable carrier matrix is a combination of paper and gelatin. In this instance a filter paper pad can be impregnated with a stable emulsion of aqueous gelatin and hydrophobic globules. Upon drying, the filter paper/gelatin carrier matrix is capable of preserving the integrity of the globules until the test means is put to its intended use.

6.2 The Hydrophobic Vehicle

The primary function of the hydrophobic vehicle is to increase the detectable response of the test means by isolating the ionophore and reporter substance from the aqueous phase produced by contact with the test sample. Thus the vehicle can be a liquid, a solid or combination thereof, provided that it increases the ability of the ionophore/ion complex and reporter substance to coexist in the hydrophobic globule. It is speculated that the hydrophobic vehicle interacts with the ionophore/ion complex in such a way as to overcome the natural tendency of charged ions to prefer an aqueous phase and in some way stabilizes the complex when formed in the hydrophobic globule. Care must be exercised to choose a vehicle which does not interfere with the interaction of the complex and the reporter. Moreover, the vehicle must preclude substantial ionic pentration of the globule unless the ion is one capable of complexing with the ionophore. However, given the present disclosure, one knowledgeable in the art will be able to choose from many compounds, or combinations thereof, which will provide a suitable hydrophobic substance.

Substances which are useful as hydrophobic vehicles include liquids which are simultaneously insoluble in water and capable of dissolving an ionophore and a reporter substance in sufficient concentration to provide a substantial response when in use. They must be relatively nonvolatile, i.e., having a boiling point of at least about 150° C., ideally at least about 200° C. Such liquids are normally oxygen donors, containing functional groups such as ether, ester, amide and the like or combinations thereof.

Typical liquids which fall into this category are tricresylphosphate, dioctylphthalate, tris-2-ethylhexylphosphate, di-2-ethylhexyl sebacate, n-butylacetylricinolate and nitrophenyl ethers such as 2-nitrophenyl octyl ether, 2-nitrophenyl butyl ether, dibenzyl ether and o-nitrophenol-2-(1,3,3-trimethyl-butyl-5,7,7-triethyl octyl ether. Mixtures of these liquids can be used.

In addition to oils and other liquid vehicles, it is likewise feasible to utilize finely divided particles (globules) of solid materials to contain and isolate the ionophore and reporter. Such globules can be formed by polymerizing a monomer in the presence of the ionophore and reporter.

The vehicle can comprise hydrophobic materials such as organic polymers which are substantially nonporous and nonpolar. These include polyvinyl fluoride, polyvinyl chloride, vinyl chloride/vinyl acetate copolymer, vinyl chloride/vinylidene chloride copolymer, vinyl chloride/vinyl acetate/vinyl alcohol terpolymer, vinylidene chloride/acrylonitrile copolymer, and polyurethane. Of course, many other polymeric materials such as silicon polymers available from Dow Corning (e.g., Q3-9595) would be suitable for use as the hydrophobic vehicle. Identification of such materials is well within the skill of the art, given the present disclosure.

6.3 Ionophores

The ionophore element of the present invention is a concept which is broad in scope, as characterized by the definition of the term in paragraph 5.1, supra. It includes multidentate cyclic compounds which contain donor atoms in their cyclic chains. Such multidentate cyclic compounds can be monocyclic or polycyclic. Alternatively, the ionophore can be an open chain containing donor atoms. Thus, included in the term are monocyclic ion-specific compounds known as coronands; polycyclic ion-specific compounds known as cryptands; open chain ion-specific compounds known as podands; and antibiotic type ionophores such as valinomycin or macratetralide actins.

6.3.1 Coronands

The coronands are monocyclic compounds containing donor atoms which are electron rich (or deficient) and which are capable of complexing with particular cations (or anions) because of their unique structures. Included in this term are the crown ethers in which the monocyclic chain contains oxygen as the donor atoms. Other coronands are compounds which contain an assortment of electron rich atoms such as oxygen, sulfur and nitrogen. Because of the unique sizes and geometries of particular coronands, they are adaptable to complexing with various ions. In so complexing, the electron rich atoms, such as the oxygens in a crown ether, orient towards the electron deficient cation. The carbon atom segments of the chain are simultaneously projected in a direction outwards from the ion. Thus, the resultant complex is charged in the center, but is hydrophobic at its perimeter. Uncharged coronands, particularly uncharged crown ethers, are preferred ionophores for the determination of potassium ion.

6.3.2 Cryptands

The cryptands are the polycyclic analogues of the coronands. Accordingly, they include bicyclic and tricyclic multidentate compounds. In the cryptands, the cyclic arrangement of donor atoms is three dimensional in space, as opposed to the substantially planar configuration of the coronand. A cryptand is capable of virtually enveloping the ion in three dimensional fashion and, hence, is capable of strong bonds to the ion forming the complex. As with the coronands, the donor atoms can include such atoms as oxygen, nitrogen and sulfur.

6.3.3 Podands

Ions can also be selectively complexed by noncyclic compounds. For example, a linear chain which contains a regular sequence of electron rich atoms such as oxygen has the capability of associating with positively charged ions to form complexes, not unlike the coronands and cryptands. The main structural difference between podands and the other two types of ionophores is the openness of the structure. Thus, podands can be subcategorized into monopodands, dipodands, tripodands, and so forth. A monopodand, therefore, is a single organic chain containing donor atoms; a dipodand is two such chains coupled by a bridge atom or group of atoms capable of variable spacial orientation; and a tripodand is three such chains attached to a central atom or group of atoms. Uncharged podands such as these are preferred ionophores for the determination of sodium and calcium ions. Simon, et al., in U.S. Pat. No. 3,957,607 discloses dipodands particularly suited to the determination of calcium or barium ions. In the present invention, a preferred ionophore is the tripodand 1,1,1-tris[1'-(2'-oxo-4'-oxo-5'-aza-5'-methyl)-dodecanyl]propane referred to herein as Sodium Ionophore I, which was found to be particularly useful in a test means for the determination of sodium ion. In fact, Sodium Ionophore I is 90 times more selective for sodium ions than the dipodand, N,N'-dibenzyl-N,ND'-diphenyl-1,2-phenylenedioxydiacetamide. [Guggi, M., Oehme, M., Pretsch, E. and Simon, W., *Helv. Achim. Acta.*, 59:2717 (1976)].

6.3.4 Specific Ionophores

Some of the ionophores which have been found to be especially useful are tabulated below along with the cations with which they are capable of selectively complexing.

Chemical names for preferred ionophores follow with their structures. Common names assigned for use herein are also noted.

| Ionophore | | Cation |
|---|---|---|
| 1,1,1-tris[1'-(2'-oxa-4'-oxo-5'-aza-5'-methyl)dodecanyl]propane | | Na+ |
| 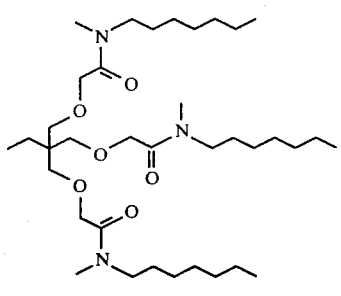 [Sodium Ionophore I] | | |
| N,N'—dibenzyl-N,N'—diphenyl-1,2-phenylenedioxydiacetamide | | Na+ |
| 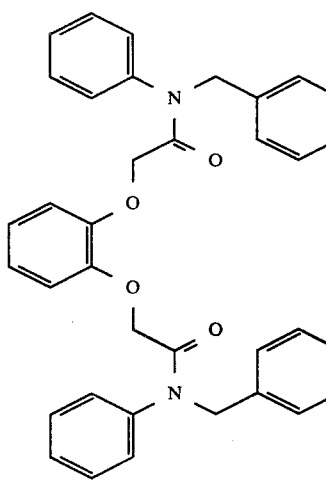 [Sodium Ionophore II] | | |
| 6,7,9,10,18,19-hexahydro-17-n-butyl dibenzo[b,k][1,4,7,10,13]pentaoxa-cyclohexadecane-18-yl-oxyacetic acid | | Na+ |
| 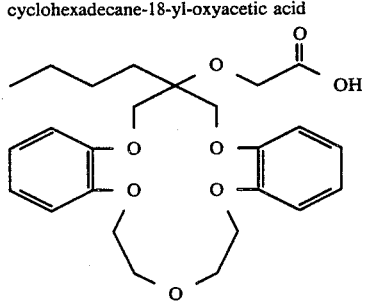 [Sodium Ionophore III] | | |
| 2,3-naphtho-1,4,7,10,13-pentaoxa-cyclopentadeca-2-ene | | K+ |
| 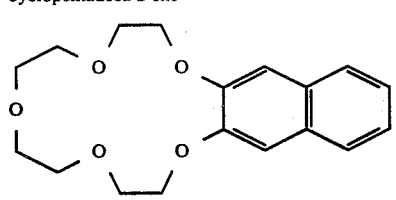 [Potassium Ionophore I] | | |
| N,N'—diheptyl-N,N',5,5-tetramethyl-3,7-dioxanonane diamide | | Li+ |

| Ionophore | Cation |
|---|---|
| -continued | |
| 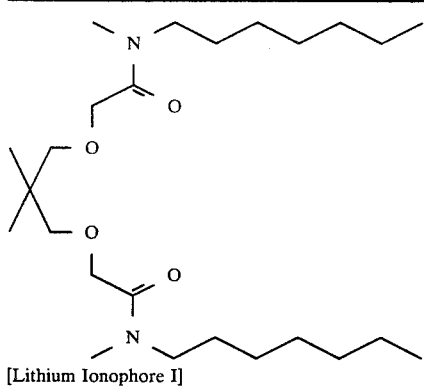  [Lithium Ionophore I] | |
| N,N'—diheptyl-5,5-dimethyl-N,N'—di(3-oxapentyl)-3,7-dioxanane diamide | Li+ |
| 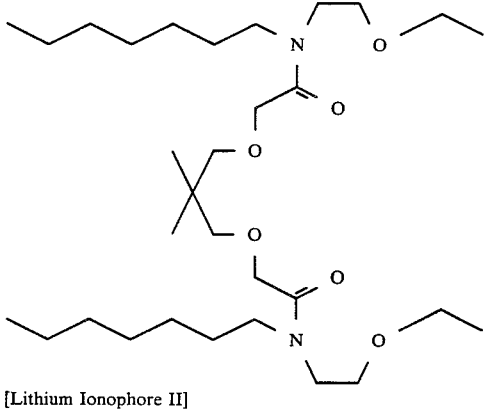  [Lithium Ionophore II] | |
| cis-N,N,N',N'—tetraisobutyl-1,2-cyclohexane dicarboxamide 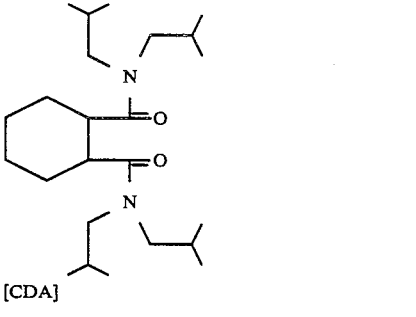  [CDA] | Li+ |
| diethyl-N,N'—[(4R,5R)-4,5-dimethyl-1,8-dioxo-3,6-dioxaoctamethylene]-bis(12-methylaminododecanoate) 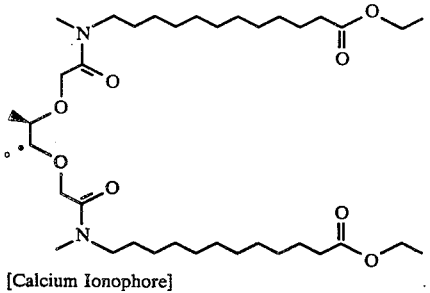  [Calcium Ionophore] | Ca++ |

Other ionophores which are useful in the present invention include those listed below:

| Ionophore | Cation |
|---|---|
| 15-crown-5 | Na+, K+ |
| Valinomycin | K+ |
| 4,7,13,16,21,24-hexaoxa-1,10-diaza-bicyclo [8,8,8]hexacosane (Kryptofix ® 222) | K+ |
| Dibenzo-18-crown-6 | K+ |
| Dicyclohexano-18-crown-6 | K+ |
| 4,7,13,18-tetraoxa-1,10-diaza-bicyclo[8,5,5]eicosane (Kryptofix ® 211) | Li+ |
| 12-crown-4 | Li+ |
| N,N'—diheptyl-N,N'—dimethyl-1,4-butanediamide | Mg++ |

Kryptofix ® is a trademark of E. Merck, Darmstadt, West Germany.

Although these specific ionophores were used advantageously in the test means of the present invention, other ionophores, or mixtures thereof, can also be used. In particular, ionophores which contain ionizable groups, such as Sodium Ionophore III, can be substituted in the formulation, so long as they have sufficient analyte-ion specificity.

6.4 The Reporter Substance

Given the presence of the ion of interest in the test solution, it is the reporter substance which provides the detectable response as a result of its interacting with the ionophore/ion complex. The reporter substance can range in composition from a single compound, which can ionize in response to the formation of the ionophore/ion complex, to a mixture of reactive species which produce a detectable product when their reaction chain is triggered by the presence of the complex. Thus, it can be seen that when no analyte-ion is present, the reporter substance remains dormant and no detectable response is observed. Alternatively, when the particular ion of interest is present, a complex is formed which interacts with the reporter and induces it to undergo a detectable change.

In the case where the reporter is a single compound, it can include a dissociable compound, such that upon dissociation a colored ionic species is formed. For the determination of a cation a particularly preferred reporter is one which contains a dissociable proton such that upon interaction of the ionophore/cation complex with the reporter, the reporter loses the proton. This proton loss causes a change in, or appearance of, a detectable response in the matrix. For example, phenolic compounds such as p-nitrophenol, are relatively colorless in the nonionized state, but are colored upon ionization. Tetrabromophenolphthalein alkyl esters have also been found to be useful reporters. Other compounds, such as those which produce more or less fluorescence upon a change in electron distribution, can also be used. Classes of fluorescent indicators and their derivatives which are useful in this invention include derivatives of fluorescein, especially fluorescein esters, 7-hydroxy coumarins, resorufins, pyrene-3-ols and flavones.

The reporter substance can also be one which can trigger a detectable response together with other components. A reaction sequence useful as the reporter substance is one which involves the dissociation of a proton from a phenol, thus initiating a coupling reaction to form a colored product. The so-called Gibbs Reaction is typical of such a reaction sequence, in which 2,5-cyclohexadiene-1-one-2,6-dihalo-4-haloimine (I) couples with a phenol (II) to form a colored reaction product (III):

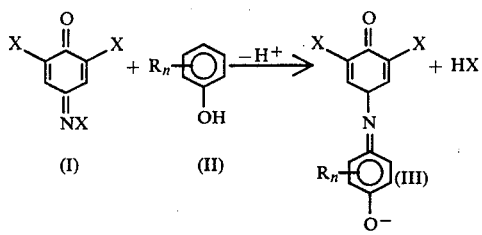

In this reaction sequence, n is 0 to 4 and R, same or different, can be any 2, 3, 5 or 6-position substitutent, or multiple substituents thereof, which will not hinder the overall reaction sequence. Thus R can be H, lower or intermediate alkyl or aryl, or R can form a fused ring system at either the 2,3- or 5,6-positions. X, same or different, is a halogen such as F, Cl, Br and I, or X can be a pseudohalogen. It is preferred that the substituents ortho to the keto group be the same and particularly preferred that they be chloro groups. Most preferred is the trichloro substituted compound. This kind of reporter substance can be utilized by incorporating compounds having the structures (I) and (II) directly with the hydrophobic globules.

Still another utilization of the Gibbs chemistry involves compounds having a structure such as (III) in its nonionized form. The formation of the ionophore/ion complex results in an interaction such that reporter substance (III) yields observable color change in and of itself. This phenomenon can be thought of as proceeding in accordance with the following reaction sequence and resonance structures:

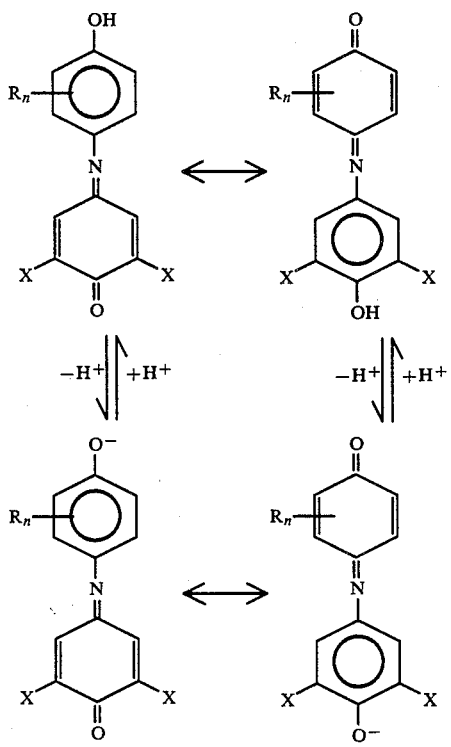

in which each R, same or different, is lower alkyl or intermediate alkyl, aryl, or a fused ring system at the 2,3- or 5,6-positions, n is 0 to 4 and X is as defined above. Especially preferred is a compound having the structure

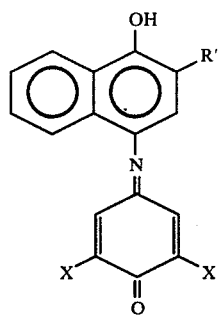

in which R' is H or lower alkyl and X is a halogen or pseudohalogen group as defined in sections 5.6 and 5.7, respectively. The case in which R' is methyl and each X is a chlorine atom has been found expecially suitable to the present invention.

Yet another preferred reporter substance is a compound having the structue

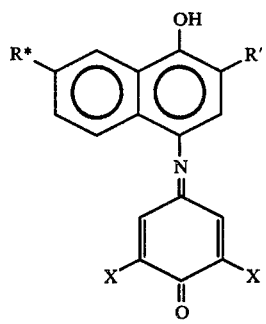

in which R* is an intermediate alkyl group, i.e., having 5 to 15 carbon atoms, and in which R' is H or lower alkyl. Compounds such as these have been found to be especially resistant to possible interference due to the presence of serum albumin in the test sample. Preferred among this type of reporter substances is 7-(n-decyl)-2-methyl-4-(3',5'-dichlorophen-4'-one)indonaphthol (referred to herein as 7-decyl-MEDPIN) in which R* is n-decyl, X is a chloro group and R' is methyl. More detailed information on the use and preparation of such compounds can be found in U.S. patent applications Ser. Nos. 493,951 and 493,981, both of which are assigned to the present assignee and are incorporated herein by reference.

6.5 Optional Components

The test means or reagent layer can optionally include wetting substances, emulsion stabilizers, oil formers, photochemical stabilizers, thickeners such as guar gum, preservatives and so forth, provided they do not interfere with the production of the detectable response. In addition buffers, light scattering centers, sodium chloride and an interferant removal substance can be incorporated with the reagent layer. Given the present disclosure, the choice of such components is well within the skill of those knowledgeable in the art. These components can be incorporated into the hydrophilic matrix or into the hydrophobic globule which ever is most suitable.

6.5.1 Buffer

A buffer or combination of buffers can be incorporated with the hydrophilic carrier matrix. Upon contact with an aqueous fluid sample, the buffer redissolves into the aqueous phase thus created, raising or lowering the pH to the desired level for the generation of the detectable response to proceed. With preferred reporters capable of losing a dissociable proton upon interaction with the ionophore/ion complex, the buffer maintains a suitable pH for the reaction to proceed.

Suitable buffers include bis[2-hydroxyethyl]iminotris[hydroxymethyl]methane; 1,3-bis[tris-(hydroxymethyl)methylamino]propane, N,N-bis-(2hydroxyethyl)glycine, tris(hydroxymethyl)aminomethane, N-[2-acetamido]-2-iminodiacetic acid; N-2-hydroxyethylpiperazine-N',3-propanesulfonic acid; 3[N-tris(hydroxymethyl)methylamino-2-hydroxypropanesulfonic acid; tetramethylammonium borate; 3-(cyclohexylamino)propane sulfonic acid and tetramethylammonium phosphate.

The preferred pH range depends on the reporter substance. Therefore, the choice of the buffer is determined by the reporter substance used and to some extent by the desired detectable response. For example, when 7-decyl MEDPIN is used as the reporter, the preferred pH range is from 6 to 8.5. However, when a reporter substance having a higher pKa for the dissociable proton is used, a higher pH range will be preferred. Similarly when a reporter having a lower pKa for the dissociable proton is used, a lower pH range will be preferred. When the detectable response is a color change, the buffer can influence the degree of such detectable response, and a particular buffer can be chosen for color intensity optimization. For example, the useful pH range for the reporter, 7-decyl MEDPIN, occurs from about pH 6 to 8.5 where the color change is from orange to blue. A higher pH, pH 8.5–10, gives shades of dark blue which are difficult to distinguish visually, and a lower pH, pH 5–6, gives shades of pale yellow, also difficult to distinguish visually. Both pH extremes could be used with instrumental analysis, although the best instrumental precision occurs at the pH range of from about 6 to 8.5. Determination of a suitable pH is a routine laboratory experiment.

6.5.2 Light Scattering Centers

In the single layer format, when instrumental reading by reflectance is used, it is advantageous to incorporate light scattering centers with the carrier matrix. The use of such centers effectively increases the precision of the assay by reducing the effect of variations in dry film thickness. Light scattering centers can be produced by incorporating insoluble, inorganic particles such as titanium dioxide particles or equivalents such as barium sulfate, calcium carbonate, magnesium oxide, aluminum oxide, zinc oxide, lead oxide, microcrystalline cellulose or talc. A working range for incorporation of titanium dioxide particles is up to about 40% weight percent of the coating emulsion; a preferred range is from about 0.5 to about 15 weight percent of coating emulsion. A particle size of less than one micron is preferred.

6.5.3 Sodium Chloride Addition to Decrease Hemotocrit Dependence

If the single layer test means is used for a whole blood electrolyte determination, sodium chloride can be incorporated with the hydrophilic carrier. The addition of approximately 0.1 to 0.2 M sodium chloride has been found to be sufficient to obviate the hematocrit dependence otherwise seen with whole blood potassium tests. The addition of salt is more advantageous in the multilayer format preferred for whole blood determinations and will be discussed more fully later.

6.5.4 Interferant Removal Substance

Body fluids normally contain many cations, such as sodium ion ($Na^+$), potassium ion ($K^+$), calcium ion ($Ca^{++}$) and magnesium on ($Mg^{++}$). Although the ionophore will usually be chosen for its selectivity for the desired analyte-ion, in some cases the presence of other cations could interfere with the coaction of the ionophore with the desired analyte-ion. For example, Sodium Ionophore I will bind sodium ion in preference to calcium ion in a ratio of approximately 4 to 1. In samples where the ratio of sodium ion to calcium ion is less than 4 to 1, it may be necessary to prevent the interaction of calcium ion with the ionophore to ensure the proper relationship between sodium ion concentration and the detectable response. An interferant removal substance can be provided to obviate this problem.

An interferant removal substance can be incorporated into the hydrophilic matrix or into the hydrophobic globules. In a preferred embodiment, the removal substance is designed to interact with an interfering cation so as to keep it in the aqueous phase formed by contact with the aqueous fluid sample, or otherwise prevent cation interaction with the ionophore in the hydrophobic globule. For example, ethylenediamine tetraacetic acid (EDTA) and ethyleneglycol bis(aminoethyl)tetraacetic acid (EGTA) are water soluble compounds which form complexes with divalent cations, such as calcium ion. If EDTA is incorporated with the hydrophilic carrier matrix of a test means for the determination of sodium ion, EDTA will preferentially bind calcium ion on contact with an aqueous sample containing sodium and calcium ions. The bound calcium ion will not substantially interfere with the formation of the ionophore/sodium ion complex in the hydrophobic globule. In addition, ionophores can be used to remove interfering cations if they are specific for the interfering ion and are water soluble or are modified chemically to increase their water solubility without decreasing their ability to interact with the interferant. For example, Sodium Ionophore III can be modified by the addition of solubilizing groups, such as ($-SO_3H$) groups, to the benzene rings to increase its water solubility without decreasing its ability to interact with sodium ion. Other compounds such as uramildiacetic acid and trans-1,2-diaminocyclohexane-N,N,N',N'-tetraacetic acid can also be used advantageously.

7. CONCENTRATION RANGES OF TEST MEANS COMPONENTS

The concentrations of the test means components are not critical to the invention provided that the concentrations of the ionophore and reporter substance are sufficient to produce the desired detectable response. For qualitative results neither the concentration of the ionophore nor the concentration of the reporter substance is tied to the concentration range of the analyte-ion to be determined.

Determination of optimum concentrations is within the ability of one skilled in the art, given the present disclosure. However, the following guidelines are provided. It is preferable that the ionophore be present in molar excess over the reporter substance (i.e., greater than 1:1 molar ratio, ionophore:reporter substance). Working concentrations of the ionophore can range from 2 gm/L to saturation in the hydrophobic globules.

The working and preferred concentration ranges for a test means responsive to potassium ion are given below. Preferred ranges are given for the determination of serum potassium by reflectance on an Ames SER-ALYZER ® reflectance photometer. These concentrations, which can be used as a starting point for the determination of useful concentration ranges for the determination of other ions with other ionophores and reporters, are given below. The concentrations of ionophore and reporter refer to concentration in the volume of organic solvent used, other concentrations are defined as grams per 100 grams of solution. The wet emulsion film thickness for the test means (or reagent layer of a multilayer test device) can be from about 25 microns to about 500 microns with the preferred wet emulsion film thickness being from about 150 microns to about 200 microns.

|  | working | preferred |
|---|---|---|
| I. Test Means (Reagent Layer) | | |
| Film thickness | 25–500 microns | 150–200 microns |
| Ionophore | 10–500 mM | 80–160 mM |
| Reporter | 10–120 mM | 30–60 mM |
| Hydrophobic Vehicle | 5–15% | 7–12% |
| Hydrophilic Carrier | 5–15% | 7–12% |
| Buffer (optional) | 0–0.5 M | 0.2–0.5 M |
| Interferant removal | | |
| substance (optional) | 0–30 gm/L | 10–20 gm/L |
| Wetting substance (optional) | 0–3 gm/L | 1–2 gm/L |
| Light Scattering | | |
| centers (optional) | 0–40% | 0.5–15% |
| Sodium chloride (optional) | 0–0.6 M | 0.5–0.15 M |
| II. Optional Multilayers | | |
| 1. Reflecting layer | | |
| titanium dioxide | 5–40% | 15–40% |
| gelatin | 1–6% | 2–6% |
| sodium chloride (optional) | 0–0.6 M | 0.05–0.5 M |
| dry coating weight | 2.5–75 gm/M$^2$ | 10–25 gm/M$^2$ |
| 2. Opacifying layer | | |
| Carbon black | 3–30% | 7–15% |
| gelatin | 1.0–12% | 1.5–6% |
| sodium chloride | 0–1 M | 0–0.6 M |
| film thickness (wet) | 10–50 microns | 15–35 microns |

Working and preferred ranges for additional layers used to prepare a multilayer device particularly suited for whole blood electrolyte determinations and for the use of sodium chloride to decrease hematocrit dependence in a whole blood determination are included in the above table for easy reference. The composition and use of such additional layers will be described more completely later in the specification.

8. THE TEST DEVICE

To prepare a single layer test device of the present invention, an emulsion is formed of finely divided hydrophobic globules containing ionophore and reporter in a hydrophilic carrier. Such an emulsion can be formed by conventional techniques such as mixing under conditions of high shear in a homogenizer or with the use of sonic power. The emulsion can also be formed by injecting (squirting) the hydrophobic vehicle in which the reporter and ionophore are dissolved through a fine orifice directly into an aqueous solution of the hydrophilic polymer. In either method, the hydrophobic vehicle can be diluted with an organic solvent which is afterward removed.

An emulsion thus formed can be coated onto a porous material capable of supporting the integrity of the globules, such as paper, and dried to form a test means. The dried coated paper can be cut into suitable sizes and affixed to an elongated support member having a upper substantially flat face, such as an oblong piece of polystyrene film. The test means piece is affixed to the flat face at one end, leaving the other end of the polystyrene to serve as a convenient handle. Alternatively the emulsion can be stripe coated directly onto a support member or coated full width onto a suitable support, dried and that support cut into suitable sizes and affixed to a convenient handle.

Useful materials for the support member include films of a myriad of plastics or polymers. Examples include such polymeric materials as cellulose acetate, polyethylene terephthalate, polycarbonates and polystyrene. The support can be opaque or it can transmit light or other energy. When the detectable response is fluorescence or when a coating is placed over the upper surface of the single layer test device to allow the sample to be wiped off, the test device can be read through a transparent support material. Preferred supports include transparent materials capable of transmitting electromagnetic radiation of a wavelength in the range of about 200 nanometers (nm) to 900 nm. The support need not, of course, transmit over the entire 200–900 nm region, although for fluorometric detection it is desirable that the support be transparent over a band wider than, or at least equal to the absorption and emission spectra of the fluorescent materials used for detection. It may also be desirable to have a support that transmits one or more narrow wavelength bands and is opaque to adjacent wavelength bands. This could be accomplished, for example, by impregnating or coating the support with one or more colorants having suitable absorption characteristics.

If necessary, the test means can be affixed to a convenient handle by any means compatible with the intended use. A preferred method is by using a double faced adhesive tape between the test means square and the support member. Double faced adhesive tapes are available from 3M Company, St. Paul, Minn.

9. USE OF THE SINGLE LAYER TEST DEVICE

The test means and devices of the present invention can be adapted for use in carrying out a wide variety of chemical analyses, not only in the field of clinical chemistry, but in chemical research and chemical process control laboratories. They are well suited for use in clinical testing of body fluids such as blood, serum and urine, since in this work a large number of repetitive tests are frequently conducted and test results are often needed a very short time after the sample is taken. In field of blood analysis, for example, the invention can be adapted for use in carrying out quantitative analysis for many of the blood electrolytes of clinical interest.

For example, preferred single layer test means formulated with Valinomycin and/or Potassium Ionophore I and 7-decyl MEDPIN is particularly useful for the determination of serum potassium. Calcium ion test means formulated with an uncharged podand and a neutral reporter having a dissociable proton can be used to determine total serum calcium.

The test means (and test device) is used by contacting it with the test sample and observing a detectable response. If the ion under analysis is present in the test sample, the complex of ionophore and ion will interact with the reporter substance and a detectable response will appear. Where the reporter substance, for example, is a dissociable compound capable of losing a proton to produce an ionic form of differing color from the parent compound, the observable response will be the appearance of, or change in, color in the test means. This appearance of, or change in, color can be monitored from either side of the device when a transparent support member is used. Where the reporter substance is a fluorophore such as fluorescein, a fluorescence spectrophotometer can be utilized to measure the detectable response formed in the test means (here, the appearance of or change in fluorescence). Other techniques useful in observing a detectable response include reflectance spectrophotometry, absorption spectrophotometry and light transmission measurements.

Various calibration techniques are applicable as a control for the analyses. For example, a sample of analyte standard solution can be applied to a separate test means as a comparison or to permit the use of differential measurements in the analysis.

10. MULTILAYER TEST DEVICE

The test means described previously can be used as the reagent layer in a multilayer test means (or device) for the determination of an ion in an aqueous fluid sample.

A preferred multilayer test device can be prepared by the addition of a reflecting layer and optionally an opacifying layer on top of the reagent layer formed by the test means containing the ionophore and reporter substance formed in finely divided hydrophobic globules.

The reflecting layer contains a material or materials in the form of insoluble inorganic particles which provides a background to aid the user in determining the detectable response in the reagent layer of the device. In a preferred embodiment for whole blood determinations the purpose of the reflecting layer is to screen the color of the red blood cells in the sample being tested from the color change to be observed by the user. A preferred substance for "screening purposes" is titanium dioxide. However, other materials can be used, for example, barium sulfate, calcium carbonate, aluminum oxide, magnesium oxide, zinc oxide, lead oxide, talc and microcrystalline cellulose. Such material is contained in the reflecting layer in an amount of from about 5 to 40 weight percent, preferably 15 to 40 weight percent, based on the total weight of the reflecting layer. Such materials generally have a particle size of less than one micron. The materials generally have a dry coating weight of 2.5 to 75 g/m$^2$, (grams per square meters), preferably 10 to 25 g/m$^2$.

In addition to the inorganic substances, the reflecting layer can contain a hydrophilic substance such as gelatin. The hydrophilic substance is contained in an amount of 2 to 8 weight percent, preferably 2.5 to 5.5 weight percent, based on the total weight of the reflecting layer. Suitable hydrophilic substances include gelatin, agarose, poly(vinyl alcohol), poly(propyleneimine), copolymers of acrylic acid, carrageenan and alginic acid. The remainder of the reflecting layer is water.

Additionally, the reflecting layer may contain one or more wetting agents (detergents) and/or one or more suspending agents. A nonlimiting example of a wetting agent which can be employed in the reflecting layer is Triton ® X-100. a test involving the determination of potassium, 0 to 0.5 weight percent Triton ®X-100 can be utilized.

Nonlimiting examples of suspending agents for use in the reflecting layer include gelatin, alginate and hydrophillic urethanes.

The reflecting layer has a dry coating weight in the range of 2.5 to 75 gm/m$^2$ (grams per square meters), preferably 10 to 25 gm/m$^2$. To prepare a multilayered device, the reflecting layer is coated on top of the reagent layer and dried at about 40° C. for about 10 minutes.

In a preferred embodiment, an opacifying layer is coated on top of the reflecting layer, i.e., the opacifying layer is optional. The opacifying layer has a wet layer thickness (thickness when applied) of 10 to 50 microns, preferably 15 to 35 microns. The opacifying layer contains substantially inert particles for imparting an opaque appearance to the layer suspended in a hydrophilic substance. Hydrophilic substance and suspending agents used can be those as described in the reflecting layer. Such particles can be, for example, carbon black particles.

The additional layers in the multilayer device can optionally include a buffer, an interferant removal substance and/or sodium chloride as described previously for the reagent layer. Prebuffering allows the test means or multilayer device to be used with unbuffered and undiluted sera or whole blood.

A multilayer device including an opacifying layer is prepared by coating the opacifying layer on top of the reflecting layer and drying the whole device again at about 40° C for about 10 minutes.

In using the multilayer device, a sample is applied on top of the uppermost layer, i.e., the reflecting layer if no opacifying layer is employed, or the opacifying layer; and the K/S of the film after a certain delay time is read from below. The multilayer format is coated on or affixed to a transparent support.

Figures 9A, 9B:
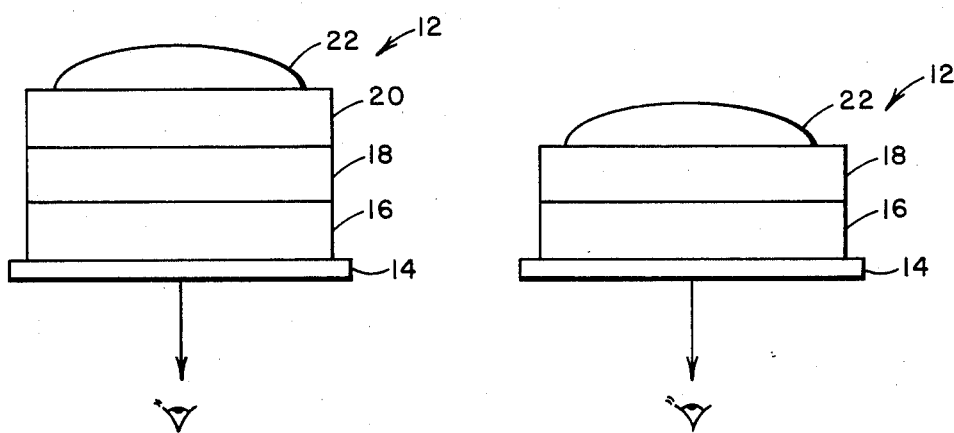

A multilayered device 12 in accordance with a preferred embodiment of the present invention is depicted in FIGS. 9a and 9b. As shown in FIG. 9b the multilayered device 12 is composed of a transparent support layer 14 on top of which is coated a reagent layer 16. A reflecting layer 18 is coated on top of the reagent layer 16. As shown in FIG. 9a on opacifying layer 20 can optionally be disposed on top of reflecting layer 18. A sample, 22, is placed on top of opacifying layer 20. Color development can be read from the bottom of layer 14 by the human eye or using a instrument such as a Glucometer ® Reflectance Photometer (Ames Division, Miles Laboratories, Inc.) which has been adapted for ion determinations.

The presence of the added reflecting layer or reflecting and opacifying layers effectively seal the reagent layer from the outside environment. Accordingly, the multilayer device protects the reagents in that without the added reflecting layer or added reflecting and opacifying layers the reagents would be exposed and, therefore, susceptible to damage due to mechanical contact. The presence of the added reflecting layer or added reflecting and opacifying layer also serve to prolong the stability of the generated color.

The use of the reflecting layer, or reflecting and opacifying layers, also provides a blocking mechanism to cells, proteins and other macromolecules, thus permitting the use of whole blood without washing or wiping the test device. In addition, due to the filtration capabilities of these layers, a multilayer test device for calcium measures ionized calcium, as bound calcium does not reach the reagent layer. Single layer and multilayer calcium test devices can be used to provide information on total calcium versus ionized calcium in a test sample.

11. EXAMPLES

Abbreviations used in the examples are as follows:

Square brackets, [], are used to designate ion concentration in millimoles per liter (mM) in the linear regression equations. All percent concentrations are given in weight per deciliter unless otherwise indicated.

Temperature:
°C.: degrees Centigrade
Length: cm: centimeters
Thickness:mil: 1 mil is equal to 25.4 microns
Weight:
gm: gram
mg: milligram
Volume:
dL: deciliter
mL: milliliter
μL: microliter
L: liter
Concentration:
mM: millimolar (millimoles per liter)
M: molar (moles per liter)
% w/v: percent weight per deciliter
% v/v: percent volume per deciliter
Ions:
$Na^{30}$: sodium ion
$K^+$: potassium ion
$Li^+$: lithium ion
$Ca^{++}$: calcium ion
$Mg^{++}$: magnesium ion Abbreviations for chemical components used are given below. The ionophore designations were assigned by the present inventors for convenience only. The name is usually based on the principal ion the ionophore was used to determine. However, the ionophores commonly respond, to varying lesser degrees, to other ions. (Structures of preferred ionophores are given in Section 6.3.4)

Ionophores

Sodium Ionophore I: 1,1,1-tris[1'-(2'-oxa-4'-oxo-5'-aza-5'-methyl)-dodecanyl]propane
Sodium Ionophore II: N N'-dibenzyl-N N'-diphenyl-1,2-phenylenedioxydiacetamide
Sodium Ionophore III: 6,7,9,10,18,19-hexahydro-17-n-butyl-dibenzo[b,k][1,4,7,10,13]centaoxacyclohexadecane18-yl-oxyacetic acid
Potassium Ionophore I: 2,3-naphtho-1,4,7,10,13-pentaoxacyclopentadeca-2-ene
Lithium Ionophore I: N,N'-diheptyl-N,N'-5,5-tetramethyl-3,7-dioxanonane diamide
Lithium Ionophore II: N,N'-diheptyl-5,5-dimethyl-N,N'-di(3-oxapentyl)-3,7-dioxanonane diamide
CDA: cis-N,N,N',N'-tetraisobutyl-1,2-cyclohexane dicarboxamide
Calcium Ionophore: diethyl-N,N'-[(4R,5R)-4,5-dimethyl-1,8-dioxo-3,6-dioxaoctamethylene]bis(12-methylaminododecanoate)

Hydrophobic Substance

NPOE: 2-nitrophenyl octyl ether
NPBE: 2-nitrophenyl butyl ether
CDA: cis-N,N,N',N'-tetraisobutyl-1,2-cyclohexane dicarboxamide
[Those below all obtained from Aldrich Chemical Co., Milwaukee, WI. unless otherside noted]
PVC: polyvinyl chloride
(low MW): low molecular weight
(very high MW): very high molecular weight
VdC/VC: vinylidene chloride/vinyl chloride copolymer (Scientific Polymer Products, Inc., Ontario, N.Y.)
VdC/AN: vinylidene chloride/acrylonitrile copolymer (Scientific polymer Products, Inc., Ontario, N.Y.)
PC - I: polycarbonate (molecular weight 20,000 to 25,000)
PC - II: polycarbonate (molecular weight 33,800)
PC - III: polycarbonate (molecular weight 38,100)

Reporter Substance 7-decyl MEDPIN: 7-(n-decyl)-2-methyl-4-(3',5'-dichlorophen-4'-one)-indonaphthol
MEDPIN: 2-methyl-4-(3',5'-dichlorophen-4'-one) indonaphthol

Buffering Substance

Bis-Tris: bis[2-hydroxyethyl]imino-tris(hydroxymethyl)methane
Bis-Tris Propane: 1,3-bis [tris(hydroxymethyl)methylamino]propane
Tris: tris(hydroxymethyl)aminomethane
Tris-Cl: tris(hydroxymethyl)aminomethane hydrochloride
ADA: N-[2-acetamido]-2-iminodiacetic acid
HEPPS: N-2-hydroxyethylpiperazine-N'-3-propanesulfonic acid
Bicine: N,N-bis[2-hydroxyethyl]glycine
TMA borate: tetramethylammonium borate
TMA phosphate: tetramethylammonium phosphate
TAPSO: 3[N-±tris(hydroxymethyl)methylamino]-2-hydroxypropane sulfonic acid (obtained from P.L. Biochemicals, Inc., Milwaukee, WI.)
CAPS: 3-(cyclohexylamino)propane sulfonic acid

Miscellaneous

THF: tetrahydrofuran
EDTA: ethylenediamine tetraacetic acid
EGTA: ethylene glycol bis(aminoethyl)tetraacetic acid (G. Fredrick Smith Chemical Co., Columbus, Ohio)
Triton ® X-100: polyethylene glycol-p isooctylphenyl ether (Sigma Chemical Co., St. Louis, MO.)
Zonyl ® FSK: 2-0-acetoxy-3-(perfluoroalkyl)-N-carboxymethyl-N,N-dimethylpropylamine (DuPont Chemical Co., Wilmington, Del.)

Zonyl ® FSN: polyethylene glycol 1-(2-perfluoroalkyl-)ethyl ether (DuPont Chemical Co., Wilmington Del.)

Zonyl ® FSB: N-perfluoroalkyl-N-carboxyethyl-N,N-dimethylamine (DuPont Chemical Co., Wilmington Del.)

Zwittergent ® 3-10: n-decyl-N,N-dimethyl-3-ammonio-1-propanesulfonate, (Calbiochem-Behring, San Diego, CA.)

Zwittergent ®3-16: N-hexadecyl-N,N-dimethyl-3-ammonio-1-propanesulfonic acid, (Calbiochem-Behring, San Diego, CA.)

Brij ® 358P: polyoxyethylene ethers of fatty alcohols (ICI United States, Inc., Wilmington, Del.)

NaDDBS: Sodium dodecyl benzene sulfonate

This invention will now be illustrated, but is not intended to be limited by the following examples.

11.1 Preparation of 7-(n-Decyl)-2-methyl-4-(3',5'-dichlorophen-4'-one)-indonaphthol The captioned compound (hereafter 7-decyl-MEDPIN) was prepared for use as a reporter substance in the present test means and test device. The reaction pathway is depicted in the following sequence, in which R* is m-decyl.

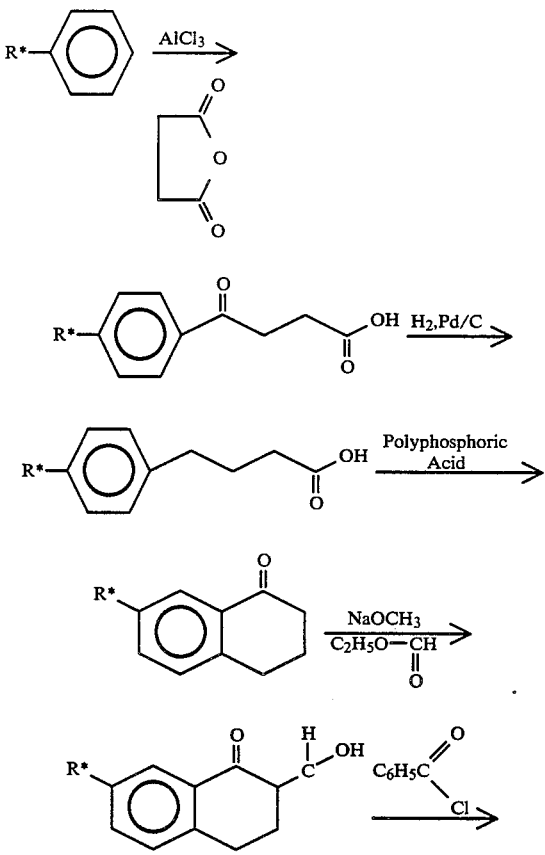

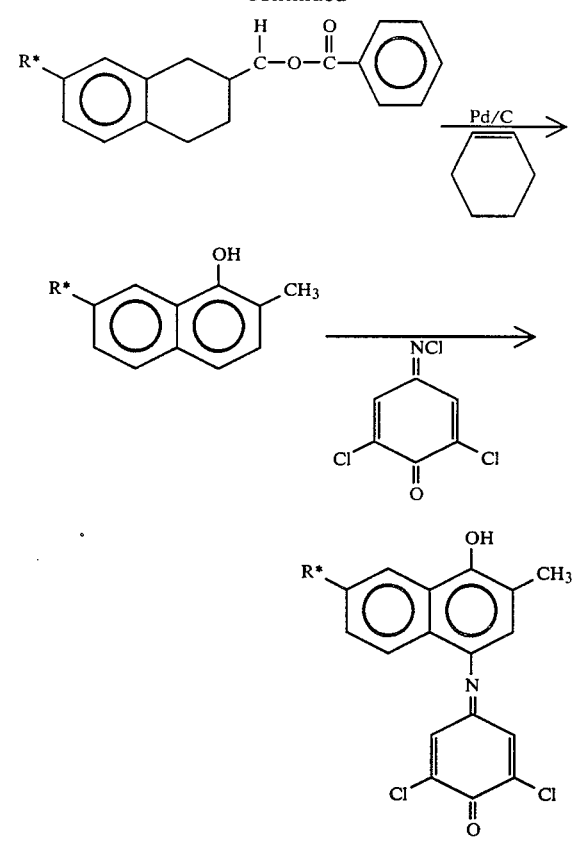

11.2 Gelatin as a Hydrophilic Carrier Matrix

A series of experiments was conducted to prepare and evaluate the test means and device of the present invention wherein gelatin was employed as the hydrophilic carrier matrix.

11.2.1 A solution of a hydrophobic vehicle containing an ionophore and a reporter substance was prepared by adding 68 mg of valinomycin obtained from Sigma Chemical Co. and 29 mg of 7-decyl-MEDPIN to 4.27 gm of NPOE with warming until solution was achieved. A buffered gelatin solution was prepared using 3.13 gm Type I gelatin (Sigma Chemical Co.) which had been dialyzed at 10° C. to remove ionic impurities, and 20.8 gm of deionized water. To this was added 0.25 ml of a buffer prepared by adjusting 1 M Tris (Sigma Chemical Co.) to pH 8 with hydrochloric acid (Baker) and then to pH 5 with acetic acid (Baker).

The emulsion was prepared by placing the oil and gelatin solutions in a 12-37 ml mini sample container for a Waring Blender (Fisher Scientific) and blending for 2 minutes at high speed. Bubbles were removed by standing 15 to 30 minutes at 40° C. under reduced pressure if necessary. This procedure was used in all further examples unless otherwise noted.

The emulsion was spread onto a polyester film support which had been pretreated to accept gelatin (40 GAB 2S, 3M Co., St. Paul, Minn.) to a thickness of $6.75 \times 10^{-3}$ inches, (#75 Meyer Rod. RDS Co., Webster N.Y.). The film was air dried, then $0.2 \times 0.4$ inch ($0.5 \times 1.0$ cm) pieces were mounted onto polystyrene handles using double-faced adhesive tape (Double Stick, 3M Co.) to form test devices suitable for use with the Ames SERALYZER® reflectance photometer. This assembly procedure was used in all further examples unless otherwise noted.

Test samples were prepared containing 0, 0.2, 0.4, 0.6, 0.8 and 1.1 mM potassium chloride, 100 mM Tris-Cl, pH 8.5. These potassium concentrations correspond to those found in plasma diluted ninefold. A 30 μL sample drop was placed on the reagent portion of the test device and incubated at 37° C. in an Ames SERALYZER® reflectance photometer (Ames Division, Miles Laboratories, Inc.) for 2.5 minutes, at which time the reflectance at 640 nm was measured. The reflectance data is tabulated below.

| $K^+$ (mM) | $(K/S)^2$ |
|---|---|
| 0 | 0.1140 |
| 0.2 | 1.2839 |
| 0.4 | 2.2822 |
| 0.6 | 3.3909 |
| 0.8 | 4.6256 |
| 1.1 | 5.9271 |

(K/S) is defined as $$K/S = \frac{(1-R)^2}{2R}$$

in which R is the fraction of reflectance from the test device, K is a constant, and S is the light scattering coefficient of the particular reflecting medium. The above equation is a simplified form of the well-known Kubelka-Munk equation (See Gustav Körtum, "Reflectance Spectroscopy", pp. 106–111, Springer Verlag, N.Y. (1969).

The above data is plotted in FIG. 1, and shows that potassium ion concentration corresponds linearly to $(K/S)^2$. Moreover, the data shows that various concentrations can be accurately measured.

11 2.2 The experiment of Example 11.2.1 was repeated using 2-methyl-4-(3',5'-dichlorophen-4'-one)indonaphthol (MEDPIN) instead of the n-decyl substituted molecule as the reporter substance. Accordingly, a solution was prepared containing 6.7 mg/ml valinomycin and 1.67 mg/ml MEDPIN in NPOE. An aqueous gelatin emulsion was prepared which contained 12% of ether solution and 7% gelatin. A film of the emulsion having a wet thickness of 0.20 inch (0.5 cm) was cast with a doctor blade onto a polyester support, dried, cut and mounted on strips of polystyrene film.

Figure 2:
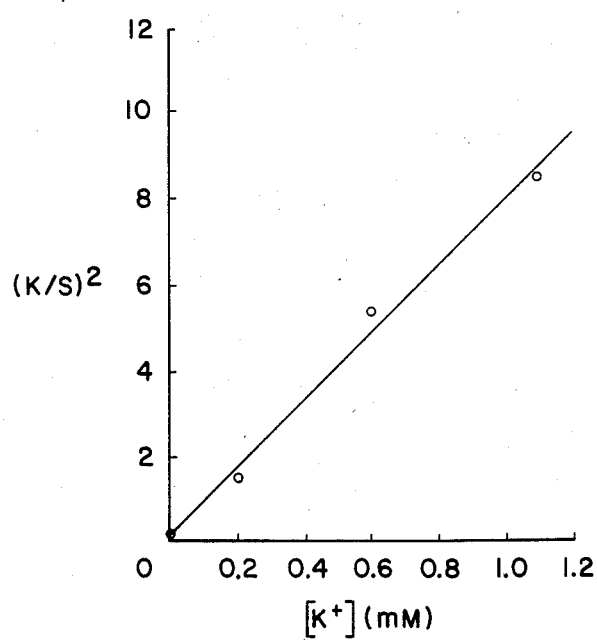

Samples of potassium chloride were prepared and the test devices evaluated as in Example 11.2.1. The reflectance data tabulated below is shown graphically in FIG. 2.

| $K^+$ (mM) | $(K/S)^2$ |
|---|---|
| 0 | 0.2048 |
| 0.2 | 1.4945 |
| 0.6 | 5.3038 |
| 1.1 | 8.4158 |

The data and its plot show a linear correlation between potassium ion concentration and $(K/S)^2$.

11.2.3 The experiment of example 11.2.1 was repeated except that 3-(n-pentadecyl)-3',5'-dichlorophen-4'-one-indophenol (DIP) was used as the reporter substance instead of 7-decyl-MEDPIN.

DIP was prepared from 3-n-pentadecylphenol and 2,6-dichloroquinone-4-chloroimide (DQCI). Equimolar amounts of these compounds were combined in acetone to achieve a theoretical concentration of about 100 mM of each. To each milliliter of solution was added 6 mL buffer (pH=10). The buffer was 100 mM CAPS. The resultant solution was adjusted to pH 2.6 with 1N HCl. The mixture was centrifuged and the precipitate dried under nitrogen atmosphere.

An aqueous gelatin emulsion was prepared containing 9.66% by weight gelatin and 12.6% by weight NPOE. Dissolved in the NPOE were valinomycin (15 mM) and DIP (25 mM).

Figure 3:
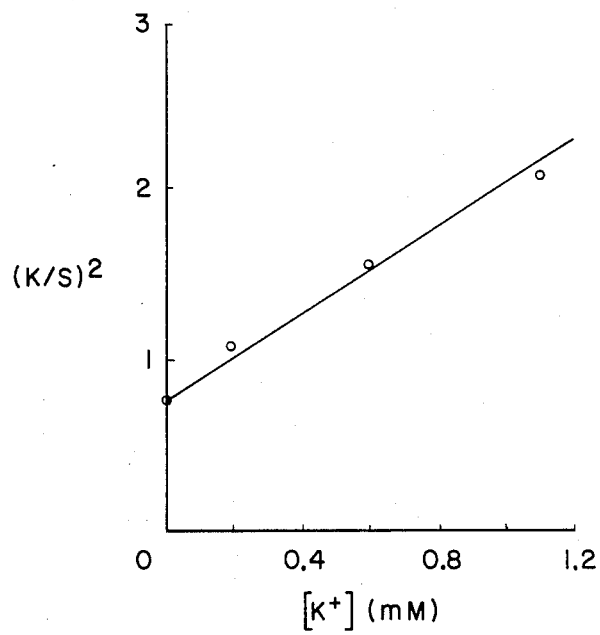

The data from evaluating the test device is tabulated below, and is portrayed graphically in FIG. 3.

| $K^+$ (mM) | $(K/S)^2$ |
|---|---|
| 0 | 0.8409 |
| 0.2 | 1.0858 |
| 0.6 | 1.5302 |
| 1.1 | 2.0794 |

The data and its plot show a linear correlation between potassium ion concentration and $(K/S)^2$.

11 3 Agarose as the Hydrophilic Carrier Matrix

A series of experiments was conducted in which the test means and device of the present invention were prepared using agarose as the hydrophilic carrier matrix.

11.3.1 A test device was prepared in which the hydrophilic carrier matrix was agarose and the hydrophobic vehicle was NPOE.

A solution was prepared by dissolving 18.6 mg valinomycin and 10.4 mg 7-decyl-MEDPIN in 1.52 mL NPOE with warming until dissolution occurred. A second solution was prepared containing 1.2 gm agarose in 40 mL distilled water at 60° C. To this solution was added 760 μL of a 1 mg/mL aqueous solution of Zwittergent® 3–10.

These solutions were emulsified as in Example 11.2.1. Next, the emulsion was cast into a 0.050 inch (0.125 cm) wet thickness film on Bruning Drafting Film using a doctor blade. Following drying at room temperature for 16 hours, test devices were made as described previously.

For evaluating the test device, aqueous solutions of potassium chloride at various concentrations were prepared. These solutions were buffered at pH 8.5 with Tris-Cl buffer. These solutions were assayed as in the previous examples with the Ames SERALYZER® reflectance photometer, and the $(K/S)^2$ values are recorded in the following table.

| $K^+$ (mM) | $(K/S)^2$ |
|---|---|
| 0 | 0.0696 |
| 0.05 | 0.7026 |
| 0.10 | 0.7026 |
| 1.15 | 1.0242 |
| 0.20 | 1.4149 |

Figure 4:
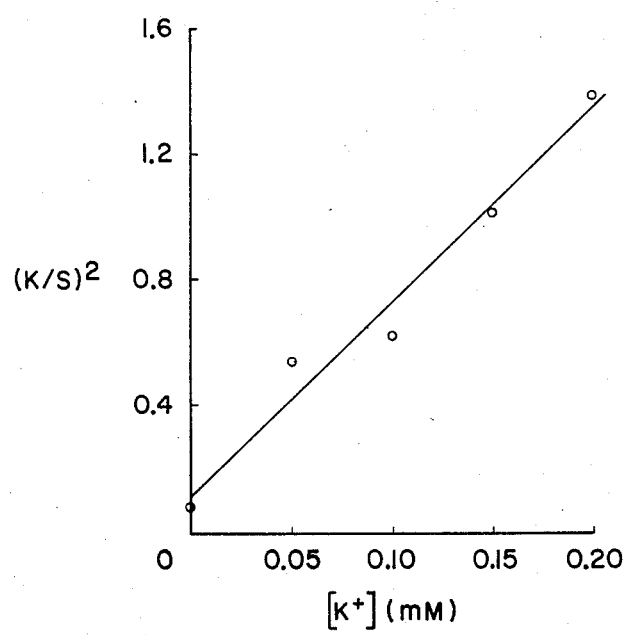

The data is plotted graphically in FIG. 4 which shows a linear correlation between potassium concentration and $(K/S)^2$. This relationship enables reflectance measurement differentiation between various concentration levels of potassium ion.

11.3.2 Valinomycin (12.8 mg) and 7-decyl-MEDPIN (5.4 mg) were dissolved in 760 μL of NPBE with warming. A second solution was prepared by adding 600 mg low gelling temperature agarose (Marine Colloids Division of FMC Corp.) to 20 mL distilled water. To this aqueous mixture was added 38 μL of a 10 mg/mL aqueous solution of Zwittergent ® 3-16.

The emulsion was cast onto Gel Bond polyester film (Marine Colloids Division of FMC Corp.) using a 0.025 inch (0.063 cm) doctor blade. Following air drying for one hour at room temperature, the film was placed in a 40° C. air oven for 15 minutes and devices were prepared.

Figure 5:
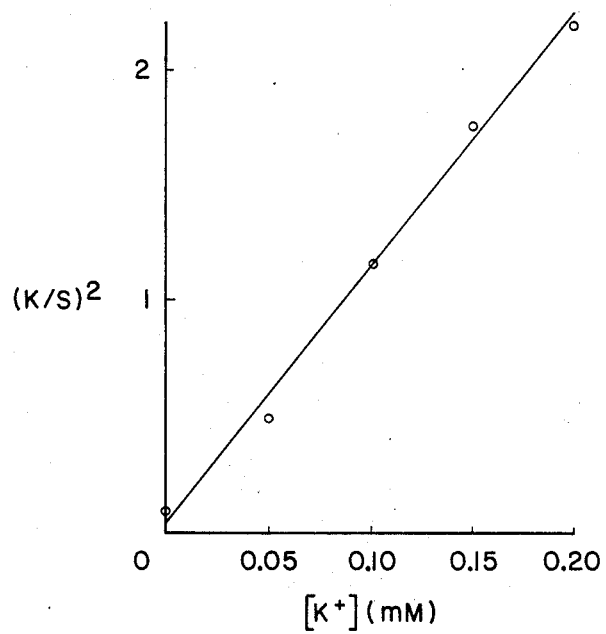

Reflectance data was collected at 640 nm (nanometers) using a SERALYZER ® reflectance photometer, and the data was converted to $(K/S)^2$ values. The results are tabulated below, and are plotted graphically in FIG. 5. They show a linear correlation between potassium ion concentration and $(K/S)^2$, which enables accurate assay of concentration.

| $K^+$ (mM) | $(K/S)^2$ |
|---|---|
| 0 | 0.0915 |
| 0.10 | 1.133 |
| 1.15 | 1.750 |
| 0.20 | 2.189 |

11.3.3 Valinomycin (12.8 mg) and 7-n-decyl-MEDPIN (5.4 mg) were dissolved in 760 μL of diethylphthalate with heating. A second solution was prepared by adding 600 mg agarose and 38 μL of a 10 mg/mL solution of Zwittergent ® 3-16 in water to 20 mL distilled water at 60° C. The two solutions were combined and emulsified.

A film of emulsion having a wet thickness of 0.05 inches (0.125 cm) was cast onto a Gel Bond film using a doctor blade. The film was allowed to stand for 2 hours at room temperature, then further dried in an air oven at 40° C. for an additional 30 minutes. Test devices were then prepared as in the above examples.

The test devices were evaluated using aqueous potassium chloride solutions containing a buffer of CAPS and LiOH (pH=10). The results are given in the following table.

| $K^+$ (mM) | (K/S) |
|---|---|
| 0 | 0.2941 |
| 0.5 | 0.5971 |
| 1.0 | 0.8909 |
| 1.5 | 1.0970 |
| 2.0 | 1.4215 |

Figure 6:
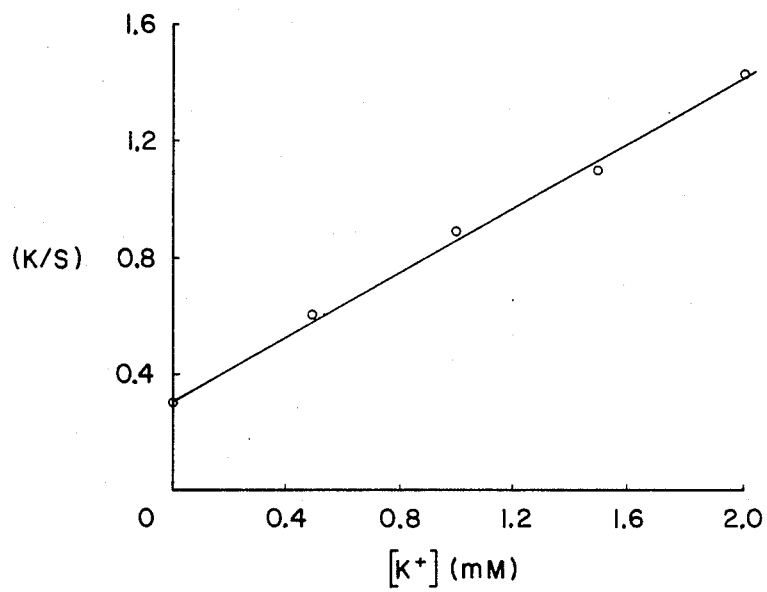

The data is plotted graphically in FIG. 6. The dose response curve enables easy differentiation between various potassium ion levels.

11.4 Paper and Hydrophilic Polymer as a Composite Carrier Matrix

Experiments were conducted to further assess ramifications of the hydrophilic carrier matrix. In the following examples, finely divided globules of a hydrophobic vehicle containing ionophore and reporter substance are entrapped in a hydrophilic matrix comprising paper and agarose.

Three stock solutions were prepared. For the first solution 28.4 mg of 7-n-decyl-MEDPIN and 71.6 mg of Potassium Ionophore I were added to 2 mL of 2-nitrophenyl octyl ether, vigorously mixed with a vortex mixer for 5 seconds, and placed for 10 to 20 minutes in a Sybron Thermolyne Dri-Bath heater set at 90° C. until all reagents were dissolved. An agarose solution was prepared by dissolving 1 gm of agarose in 20 mL of water at 80° C. A zwitterionic detergent solution was prepared by dissolving 50 mg of Zwittergent ® 3-10 in 20 mL of water.

A reagent emulsion was prepared from 0.8 mL of the first solution, 12.0 mL of the agarose solution, 0.8 mL of the detergent solution and 1.4 mL of distilled water. The emulsion was applied to Whatman 31 ET paper using a No. 75 Meyer Rod. The paper was dried in a 60° C. oven for 20 minutes and then used to make test devices.

Testing of the strips was done by measuring the diffuse reflectance at 640 nm of the reacted reagent pad using a SERALYZER instrument. Five aqueous solutions of potassium chloride buffered at pH 9.0 with 100 mM borate buffer were used as samples. At each level of potassium, triplicate strip reactivities were measured and the mean calculated. The results were tabulated below.

| $K^+$ (mM) | (K/S) |
|---|---|
| 0.08 | 0.4297 |
| 0.12 | 0.4825 |
| 0.16 | 0.5494 |
| 0.20 | 0.5943 |
| 0.24 | 0.6663 |

Figure 7:
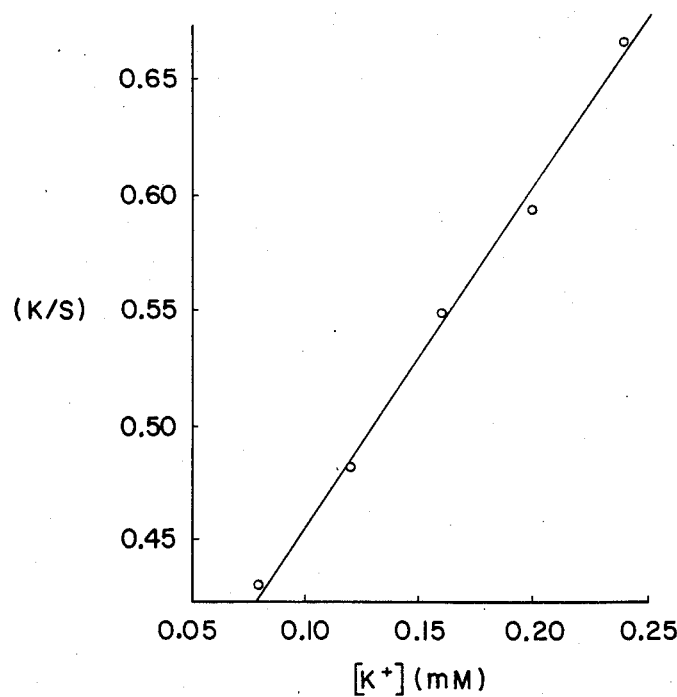

The results indicate excellent assay results for varying potassium ion concentrations, as shown by the plot of the above data in FIG. 7.

11.5 Use of Titanium Dioxide as an Ingredient of the Carrier Matrix

An experiment was conducted in which the test means and device of the present invention were prepared using titanium dioxide as an additional ingredient in the composite carrier matrix. The results show improved capability in determining ions in a test sample.

An emulsion of NPOE (12.6% by weight) and gelatin (9.6% by weight) in water was prepared. Prior to emulsification, the NPOE was made 15 mM in 7-decyl-MEDPIN and valinomycin, respectively. After emulsifying the NPOE/gelatin mixture, the resultant emulsion was spread onto a polyester film treated to accept gelatin (40 GAB 2S, 3M Co., St. Paul, Minn.). The films were spread to a wet thickness of 6.75 mils (171.5 microns) (#75 Mayer Rod), 15 mils (381 microns) (doctor blade) and 30 mils (752 microns) (doctor blade). The films were dried at room temperature for about 30 mintues.

A second set of films were prepared as above except that 0.75% by weight of titanium dioxide powder was included (0.5 micron particle size, NL 2030 available from NL industries). The films were spread on 40 GAB 2S polyester film to wet thickness of 3.6 mils (#40 Mayer Rod), 6.75 mils (#75 Mayer Rod), 15 mils (doctor blade) and 30 mils (doctor blade). Test devices were prepared.

Test samples were prepared containing 0.2, 0.6, 1.1 and 3.3 mM potassium chloride in 100 mM TRIS buffer (pH 8.0). An aliquot of each test sample (30 μL) was applied to a separate film, and the change in reflectance monitored for 130 to 150 seconds with a SERALYZER. The reflectance values were converted to (K/S) as in Example 11.2. The resultant (K/S) values are recorded in the following table.

| TiO₂ (% by weight) | Thickness (mils) | Response (K/S) of Films to Potassium [K⁺] mM | | | |
|---|---|---|---|---|---|
| | | .2 | .6 | 1.1 | 3.3 |
| 0 | 6.75 | .6300 | 1.1465 | 1.7825 | 2.970 |
| 0 | 15.0 | .8470 | 1.5780 | 2.1685 | 3.600 |
| 0 | 30.0 | 1.0265 | 1.8555 | 2.545 | 4.029 |
| + .75% TiO₂ | | | | | |
| 0.75% | 3.60 | .1781 | .2833 | .3596 | .5474 |
| 0.75% | 6.75 | .1984 | .3259 | .4144 | .6163 |
| 0.75% | 15.0 | .1924 | .3147 | .4064 | .6052 |
| 0.75% | 30.0 | .1910 | .2919 | .3794 | .5791 |

The data shows that varying thicknesses of films containing titanium dioxide have little effect on (K/S) for a particular potassium ion concentration; whereas relatively large differences are observed with varying film thickness absent titanium dioxide in the formulation.

11 6 Serum Potassium Determination

Figure 8:
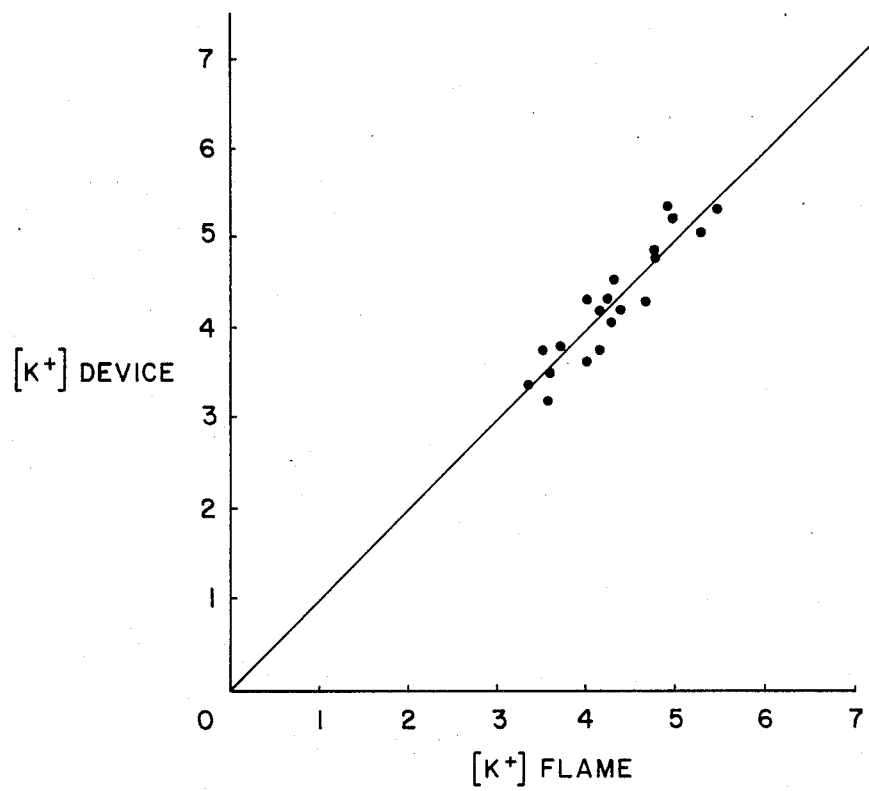

A single layer test means for determination of serum potassium was formulated by emulsifying NPOE containing 120 mM Potassium Ionophore I and 60 mM 7-decyl-MEDPIN in a hydrophilic carrier matrix containing 12 gm % gelatin, 10 mM Tris buffer (pH 8) and 0.05% (w/v) NaDDBS. The final emulsion contained 12 gm of the NPOE mixture per 100 gm of emulsion. The emulsion was spread on polyester to a wet thickness of 6.75 mils with a doctor blade, dried and used to assemble test devices. The serum samples were diluted 1 to 27 with 0.05M Tris buffer, pH 8.0. The samples were contacted with the test means and read after approximately 4 minutes on a Ames SERALYZER ® reflectance photometer from the sample side. The reference method employed was the flame photometer. Results are shown in FIG. 8. The correlation between the device reading and the flame photometer is good. Least squares regression analysis on the data from twenty-one samples gave:

$$Y = 1.0002[K^+] + 0.00388;$$

regression coefficient = 0.9611
standard error = 0.25 mM

11.7 Magnesium Single Layer

A single layer test means for the determination of magnesium ion can be prepared as follows. A solution is prepared containing 2.5 gm of magnesium ionophore (N,N'-diheptyl-N,N'-dimethyl-1,4-butanediamide, available from Fluka Chemical Co.), 0.050 gm of 7-decyl MEDPIN and 2.5 gm of NPO!E. An emulsion of 1.25 gm of this solution in a hydrophobic carrier is prepared. The hydrophilic carrier is composed of

| gelatin | 1.00 gm |
|---|---|
| Tris buffer (100 mM, pH 8.5) | 0.05 mL |
| Triton ® X-100 | 0.05 mL |
| NaDDBS | 0.05 mL |

The emulsion is spread on a plastic support such as a polyester to a thickness of 0.25 mil (6.35 microns) and dried.

Test means thus formed are expected to produce good response to magnesium ion. If calcium ion interference is possible, an appropriate level of EGTA can be incorporated with the hydrophilic carrier to selectively bind any calcium ion in the sample. For clinical serum samples, 2 to 3 mM EGTA would be appropriate.

11.8 Multilayer Potassium—Correlation of Serum and Whole Blood Measurements with the Reference Method The potassium ion concentration determined from a two layer test device was compared to the determination of potassium with a flame photometer reference method. Blood from fifteen normal subjects was drawn and the potassium concentration determined with the device, using the reflectance measured from 155–180 seconds. Serum was prepared by centrifugation and assayed with the device in the same way. Aliquots were also assayed by the flame photometer reference method.

The reagent layer was prepared by emulsifying the hydrophobic vehicle, NPBE, containing 120 mM Potassium Ionophore I and 30 mM 7-decyl MEDPIN with a hydrophilic carrier and with the aid of butananedioic acid, dodecyl-4,4'-[(1-methylethylidene)di-4,1-cyclohexanediyl] ester. The emulsion was coated and dried before the reflective layer was applied.

| Reagent Layer: | |
|---|---|
| hydrophobic vehicle | 8.3% |
| gelatin | 8.3% |
| oil former | 0.042% |
| polystyrene sulphonate | 0.02% |
| Tris-Cl (pH 7.5) | 0.2 M |
| Wet Thickness: | 375 microns |
| Reflective Layer: | |
| gelatin | 2.75% |
| titanium dioxide | 19% |
| Wet Thickness: | 82 microns |

Figure 10A:
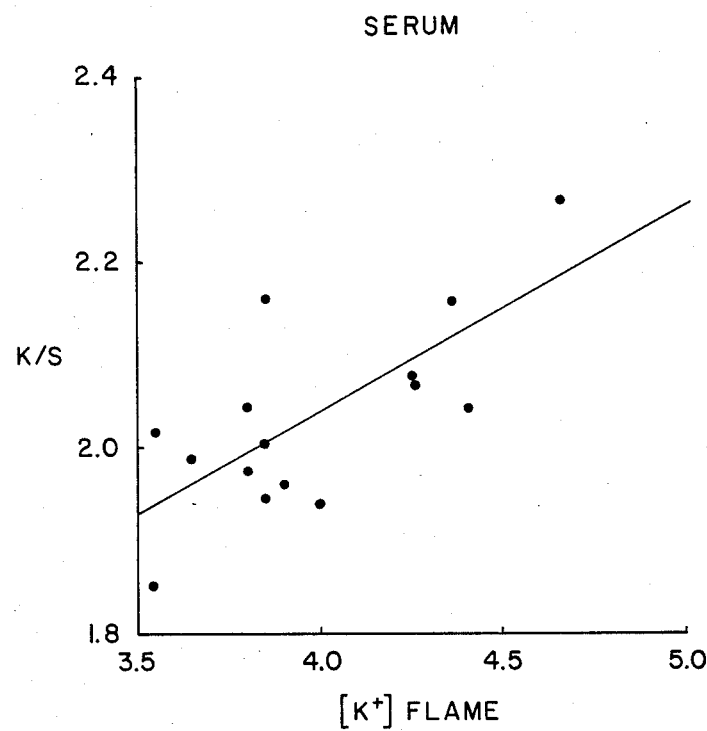
FIG. 10 shows comparative data for a multilayer device, in millimolar potassium ion concentration [K+], compared to results for the reference flame photometry.
Figure 10B:
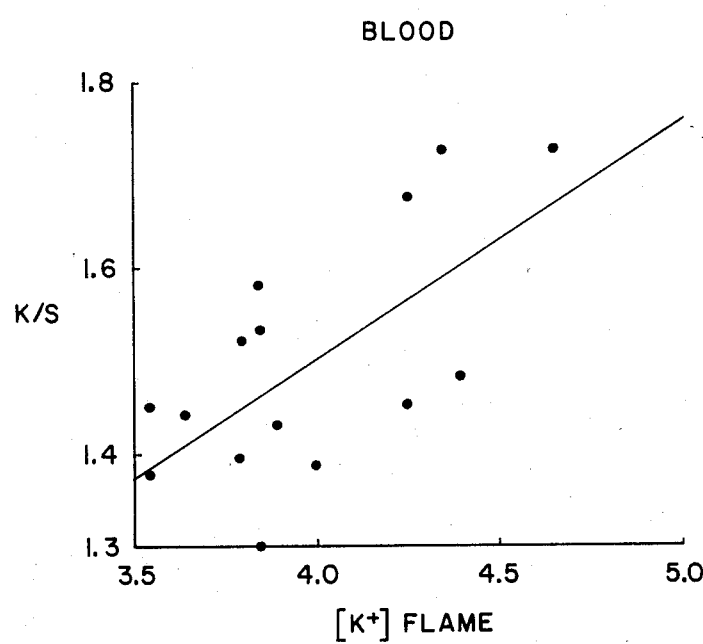

Percentages given are gm per 100 ml of the coating solution. Test devices were prepared with a transparent support and the reflectance measured through the support with a SERALYZER ®. The data is shown below and plotted in the graphs shown in FIG. 10.

| Sample # | Reference[K⁺] Concen. mM | Response from Device, K/S | |
|---|---|---|---|
| | | Blood | Serum |
| 1 | 4.40 | 1.484 | 2.043 |
| 2 | 3.80 | 1.399 | 1.977 |
| 3 | 3.85 | 1.536 | 2.160 |
| 4 | 3.80 | 1.525 | 2.046 |
| 5 | 3.65 | 1.444 | 1.992 |
| 6 | 3.55 | 1.380 | 2.020 |
| 7 | 3.55 | 1.451 | 1.854 |
| 8 | 3.85 | 1.585 | 2.004 |
| 9 | 3.90 | 1.433 | 1.964 |
| 10 | 3.85 | 1.303 | 1.949 |
| 11 | 4.25 | 1.456 | 2.079 |
| 12 | 4.00 | 1.391 | 1.944 |
| 13 | 4.35 | 1.731 | 2.162 |
| 14 | 4.65 | 1.734 | 2.270 |
| 15 | 4.25 | 1.679 | 2.074 |

For blood, the correlation equation is:

$$K/S = 0.258 [K^+] + 0.474;$$

regression coefficient = 0.653
Standard error = 0.10 K/S
For Serum: $K/S = 0.226 [K^+] + 1.138;$ regression coefficient=0.713
standard error=0.076 K/S The results clearly show a good correlation between the response measured with the device and the concentration of potassium ion in both blood and serum.

11.9 Addition of Sodium Chloride to Obviate Hematocrit Dependence of a Whole Blood Potassium Test The volume fraction of blood volume occupied by red blood cells, (the hematocrit) is normally 40–42%. Inside the red blood cell, the concentration of potassium ion is approximately 120 mM whereas that in the serum is approximately 4 mM. Hence a potassium determination on whole blood is sensitive to a very small degree of red blood cell destruction (hemolysis).

While the hematocrit is usually 40 to 42%, it can range from 30 to 70% in pathological states. It was found that the response of a potassium test device was sensitive to the value of the hematocrit. This could lead to erroneous measured values of potassium ion concentration. A series of devices were prepared having a substantially common formula, but varying in the amount of sodium chloride (NaCl) added to the reagent or the reflective layers.

An emulsion of an oil phase dispersed in a continuous aqueous phase containing gelatin was prepared using a high shear emulsifier. The oil former used was the same as that used in Example 11.8.

The composition of the oil phase was

| | |
|---|---|
| Potassium Ionophore I | 120 mM |
| 7-decyl MEDPIN | 30 mM |
| oil former | 0.6% |
| NPBE | remainder |

The final composition of the emulsion was

| | |
|---|---|
| Oil phase | 8.31% |
| Gelatin | 8.31% |
| Polystyrene sulfonic acid | 0.0207% |
| Tris-Cl buffer pH 7.5 | X |
| NaCl | (shown on table) |

Percentages given are weight per volume of the phase referred to. The concentration of Tris-Chloride used as the buffer, X, in device 1 was 0.2 M; the remaining devices were prepared with 0.166 M Tris-Cl buffer. The reagent layer was cast to a wet thickness of 175 microns on a polyester backing. The reflective layer contained

| | |
|---|---|
| titanium dioxide | 19% |
| gelatin | 2.75% |
| Tris-Cl buffer pH 7.5 | X |
| Triton X-100 | 0.03% |
| NaCl | (shown on table) |

The concentration of Tris-Cl buffer, X, used in device 1 was 0.1 M; the remaining devices were prepared with 0.062 M Tris-Cl Buffer. The reflective layer was then spread on the dried reagent layer to a wet thickness of 82 microns.

| Formulation | Concentration NaCl (M) | | |
|---|---|---|---|
| | [Reagent] Layer | [Reflective] Layer | Overall* |
| 1 | 0 | 0 | 0 |
| 2 | 0.05 | 0.05 | 0.05 |
| 3 | 0.15 | 0.05 | 0.12 |
| 4 | 0.05 | .5 | 0.19 |
| 5 | 0.15 | .5 | 0.26 |

The overall(*) concentration of sodium chloride was calculated by adding the salt concentration in each The overall (*) concentration of sodium chloride was calculated by adding the salt concentration in each layer from the equation:

$$\text{Overall} = \frac{[\text{reagent}] + [\text{reflective}]}{(\text{reagent} + \text{reflective layer}) \text{ thickness}}$$

wherein [reagent] is found by multiplying the reagent layer thickness by the sodium chloride concentration in that layer and [reflective] is found by multiplying the reflective layer thickness by the sodium chloride concentration in the reflecting layer.

Test devices were prepared and the potassium ion response measured as described previously. Samples of varying hematocrit were prepared. A high hematocrit sample (about 60%) was generated by gentle centrifugation and removal of some serum. A range of samples having the same potassium ion concentration but varying hematocrit was prepared by adding back different amounts of the autologous serum.

Figure 11:
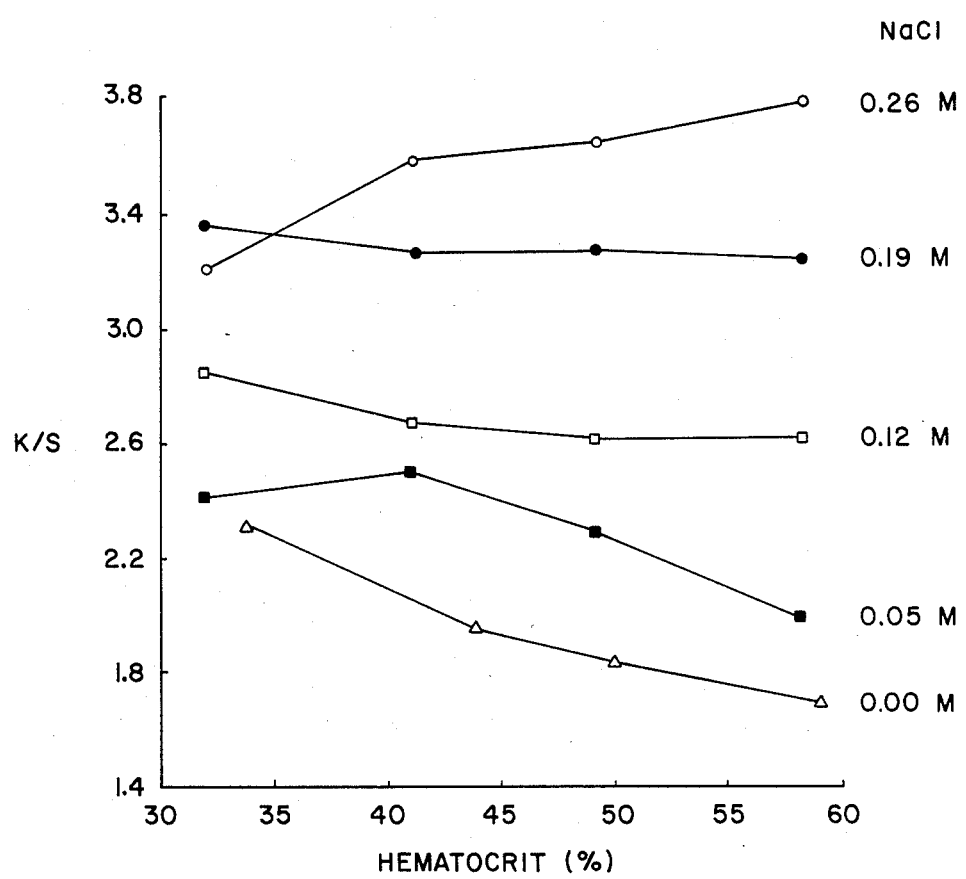
FIG. 11 shows the decrease of hematocrit dependence of a whole blood potassium determination when sodium chloride is incorporated into the multilayer test device.

Assay of the samples with the five device formulations showed that with less than about 0.1 M sodium chloride, the potassium ion response decreases with increasing hematocrit, with too much sodium chloride the response increases. The addition of from about 0.1 to about 0.2 M overall sodium chloride provides a test device essentially independent of hematocrit. These results are shown in FIG. 11. The overall molar concentration of sodium chloride in the test device formulation is marked for each response curve.

11.10 Multilayer Calcium Test Device

A multilayer test device for the determination of calcium ion can be formed with three layers: a reagent layer, a reflective layer and a opacifying layer.

The composition of the layers would be as follows:

| | | |
|---|---|---|
| Reagent layer: | Oil | 1.25 gm |
| | gelatin | 1 gm |
| | Tris buffer (100 mM, pH 8) | 8 gm |
| | Triton ® X-100 | 0.05 mL |
| | NaDDBS | 0.05 mL |
| Reflective layer: | gelatin (10% w/v in Tris buffer) | 60 mL |
| | Titanium dioxide | 36 gm |
| | Sodium hexametaphosphate | 0.1 gm |
| | Triton ® X-100 | 1 mL |
| | NaDDBS | 0.25 mL |
| Opacifying layer: | Carbon Black | 15 gm |
| | gelatin (10% w/v in Tris buffer) | 60 mL |
| | NaDDBS | 0.5 mL |
| | distilled | 30 mL |

-continued

| water |
| --- |

The oil used in the reagent layer if composed of 0.1 gm Calcium Ionophore I, 0.05 gm 7-decyl MEDPIN and 5 mL NPOE. The carbon black used is available from Degussa Corp., Teterboro, N.J. under the trademark DERUSSOL Z35. The oil and the rest of the reagent layer is spread on a transparent plastic support with a Meyer's Rod to a wet thickness of 6.75 mil. (171.45 microns) and allowed to dry.

The reflective layer is prepared by blending the ingredients above and spreading the mixture on the dried reagent layer to a wet thickness of 3.60 mil (91.44 microns).

The two layered test means thus formed is again dried. The test means could be used at this point for a serum calcium ion determination.

The opacifying layer is then applied by blending the above ingredients and spreading on to the reflective layer of the dried two-layer device to a wet thickness of 1.25 mil (32 microns). For convenience the multilayered test means is mounted on a rigid support member such as a transparent polystyrene which permits either visual or instrumental determination from the side of the device opposite the sample application. In use, one drop (approximately 50 microliters) of sample, (either whole blood or serum) is applied to the opacifying layer. Color development can be viewed through the transparent support and compared with a suitable color chart or preferably is read by reflectance at 640 nm by the Ames SERALYZER ® reflectance photometer.

Obviously many other modifications and variations can be made without departing from the spirit and scope thereof the invention.

What is claimed is:

1. A test means for determining the presence of an ion in an aqueous test sample, the test means comprising a hydrophilic carrier matrix incorporated with finely divided globules of a hydrophobic vehicle, said vehicle containing
   an ionophore capable of forming a complex with a specific ion to be determined, and
   a reporter substance capable of interacting with the complex of the ionophore and the ion to produce a detectable response.

2. The test means of claim 1 which additionally includes a buffer incorporated in the hydrophilic carrier matrix.

3. The test means of claim 1 which additionally includes an interferant removal substance which substance is capable of removing interfering ions.

4. The test means of claim 1 in which the test sample is whole blood and in which the hydrophilic carrier is additionally incorporated with sufficient sodium chloride to impart hematocrit independence to the ion determination.

5. The test means of claim 1 in which the hydrophilic carrier matrix is additionally incorporated with light scattering centers.

6. The test means of claim 5 in which the light scattering centers are composed of titanium dioxide particles.

7. The test means of claim 1 in which the hydrophilic carrier matrix is a hydrophilic polymer.

8. The test means of claim 7 in which the hydrophilic polymer is gelatin.

9. The test means of claim 7 in which the hydrophilic carrier matrix additionally comprises a porous material capable of supporting the integrity of the finely divided globules.

10. The test means of claim 9 in which the porous material is paper.

11. The test means of claim 1 in which the specific ion to be determined is a cation and the reporter is a neutral compound having a dissociable proton, which proton is capable of dissociating upon interaction of the reporter with the complex of the ionophore and the cation to produce a detectable response.

12. The test means of claim 11 in which the reporter substance is one capable of producing the appearance of, or change in, fluorescence in the presence of the complex of the ionophore and cation.

13. The test means of claim 12 in which the reporter substance is fluorescein or a derivative thereof.

14. The test means of claim 11 in which the reporter is one capable of producing the appearance of, or change in, color in the presence of the complex of the ionophore and the cation.

15. The test means of claim 14 in which the reporter substance is a compound having the structure in which X is a halogen or pseudohalogen; in which each R, same or different, is a 2-, 3-, 5-, or 6-position substituent, or multiple substituents thereof selected from a lower alkyl, intermediate alkyl, aryl or a fused ring at the 2,3-or 5,6-position; and n is 0 to 4.

16. The test means of claim 14 in which the reporter substance is a compound having the structure in which R' is H or lower alkyl, R* is H or intermediate alkyl and X is a halogen or pseudohalogen.

17. The test means of claim 16 in which R' is methyl and R* is n-decyl.

18. A method for preparing a test means for determining the presence of an ion in an aqueous test sample, the method comprising the steps of:

(a) forming a first mixture of water and a hydrophilic polymer;
(b) forming a second mixture of a hydrophobic vehicle, an ionophore capable of forming a complex with a specific ion to be determined and a reporter substance capable of interacting with the complex of the ionophore and the ion to produce a detectable response,
(c) combining the first and second mixtures to produce a stable emulsion of finely divided globules of the second mixture in the first mixture,
(d) coating the emulsion onto a porous material capable of supporting the integrity of the finely divided globules; and
(e) evaporating the water from the emulsion to produce a hydrophilic carrier matrix incorporated with finely divided globules of the second mixture.

19. The method of claim 18 in which the porous material is paper.

20. A method for preparing a test device for determining the presence of an ion in an aqueous test sample, the method comprising the steps of:
(a) forming a first mixture of water and a hydrophilic polymer;
(b) forming a second mixture of a hydrophobic vehicle, an ionophore capable of forming a complex with a specific ion to be determined and a reporter substance capable of interacting with the complex of the ionophore and the ion to produce a detectable response;
(c) combining the first and second mixtures to produce a stable emulsion of finely divided globules of the second mixture in the first mixture,
(d) coating the emulsion onto a support member having an upper, substantially flat face; and
(e) evaporating the water from the emulsion to produce a hydrophilic carrier matrix incorporated with finely divided globules of the second mixture, the emulsion being thereby affixed to the flat face of the support member.

21. A multilayer test device for determining the presence of an ion in an aqueous test sample, comprising:
(a) a reagent layer including a hydrophilic carrier matrix incorporated with finely divided globules of a hydrophobic vehicle, the globules containing
(i) an ionophore capable of forming a complex with a specific ion to be determined, and
(ii) a reporter substance capable of interacting with the complex of the ionophore and the ion to produce a detectable response; and
(b) a reflecting layer disposed on top of the reagent layer and in laminar relationship thereto, the reflecting layer including one or more materials which act as a background in order to facilitate the determination of a detectable response in the reagent layer.

22. The multilayer test device of claim 21, wherein the background material of the reflecting layer is titanium dioxide.

23. The multilayer test device of claim 21 additionally comprising a transparent support member disposed on the reagent layer on the side opposed to the reflecting layer.

24. The multilayer test device of claim 21, in which the reflecting layer additionally includes a hydrophilic polymer.

25. The multilayer test device of claim 24, in which the reflecting layer additionally includes a buffer.

26. The multilayer test device of claim 24 in which the sample is whole blood and which additionally includes sufficient sodium chloride, incorporated in either the reagent layer, the reflecting layer or both, to impart hematocrit independence to the ion determination.

27. The multilayer test device of claim 21 additionally comprising an opacifying layer in laminar relationship to the reflecting layer and disposed on top of the reflecting layer, the opacifying layer containing particles for imparting an opaque appearance to the opacifying layer.

28. A multilayer test device of claim 27, in which the opacifying particles are particles of carbon black.

29. The multilayer test device of claim 28 in which the sample is whole blood and which additionally includes sufficient sodium chloride incorporated in any or each of the layers to impart hematocrit independence to the ion determination.

30. The multilayer test device of claim 28, in which the opacifying layer additionally comprises a hydrophilic polymer.

31. The multilayer test device of claim 30 in which the hydrophilic polymer is gelatin.

32. A multilayer test device of claim 30, in which the opacifying layer additionally comprises a buffer.

33. A process for the determination of unbound calcium in an aqueous fluid sample, comprising the steps of:
(a) contacting the multilayer test device of claim 21 with an aqueous fluid sample; and
(b) determining the response in the reagent layer.

* * * * *